(12) United States Patent
Lunsford et al.

(10) Patent No.: US 8,241,210 B2
(45) Date of Patent: *Aug. 14, 2012

(54) VESSEL RETRACTOR

(75) Inventors: John P Lunsford, San Carlos, CA (US); Charles J Adam, San Jose, CA (US); John W Davis, Mountain View, CA (US); Albert K Chin, Palo Alto, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/969,318

(22) Filed: Jan. 4, 2008

(65) Prior Publication Data

US 2008/0103365 A1     May 1, 2008

Related U.S. Application Data

(63) Continuation of application No. 10/807,368, filed on Mar. 22, 2004, now Pat. No. 7,326,178, which is a continuation of application No. 10/218,475, filed on Aug. 12, 2002, now Pat. No. 6,752,756, which is a continuation of application No. 09/490,552, filed on Jan. 25, 2000, now Pat. No. 6,432,044, which is a continuation of application No. 09/227,393, filed on Jan. 8, 1999, now abandoned, which is a continuation-in-part of application No. 09/102,723, filed on Jun. 22, 1998, now Pat. No. 5,895,353.

(51) Int. Cl.
*A61B 17/02* (2006.01)

(52) U.S. Cl. .................................................. 600/209
(58) Field of Classification Search .............. 600/201, 600/203, 204, 205, 208, 209, 217
See application file for complete search history.

(56) References Cited

U.S. PATENT DOCUMENTS

| 1,083,386 A | 1/1914 | Chapman |
| 1,422,826 A | 7/1922 | Brown |
| 1,683,708 A | 9/1928 | Wappler |

(Continued)

FOREIGN PATENT DOCUMENTS

AU     199935034 A1     6/1999

(Continued)

OTHER PUBLICATIONS

Initial Expert Report of Paul Mitiguy, Oct. 31, 2008.

(Continued)

*Primary Examiner* — Nicholas Woodall
(74) *Attorney, Agent, or Firm* — Vista IP Law Group, LLP

(57) ABSTRACT

A surgical apparatus includes an elongate cannula having a lumen extending therein between proximal and distal ends, a retractor disposed to slide within the lumen to extend a distal end thereof beyond the distal end of the cannula, an angling device connected to the retractor near the distal end of the retractor and extending within the cannula toward the proximal end thereof for selectively deflecting the distal end of the retractor away from a central axis of the cannula in response to manual manipulation of the angling device from near the proximal end of the cannula, wherein the distal end of the retractor is configured to move, upon extension, an object away from the central axis of the cannula.

14 Claims, 16 Drawing Sheets

U.S. PATENT DOCUMENTS

| | | |
|---|---|---|
| 1,727,495 A | 9/1929 | Wappler |
| 1,731,069 A | 10/1929 | Herman |
| 1,741,461 A | 12/1929 | Herman |
| 1,798,902 A | 3/1931 | Raney |
| 1,867,624 A | 7/1932 | Hoffman |
| 1,881,250 A | 10/1932 | Tomlinson |
| 1,978,495 A | 10/1934 | Landau |
| 2,001,169 A | 5/1935 | Wallace |
| 2,002,594 A | 5/1935 | Wappler |
| 2,004,559 A | 6/1935 | Wappler et al. |
| 2,011,169 A | 8/1935 | Wappler |
| 2,012,937 A | 9/1935 | Beuoy |
| 2,028,635 A | 1/1936 | Wappler |
| 2,162,681 A | 6/1939 | Ryan |
| 2,220,720 A | 11/1940 | Jett |
| 2,227,727 A | 1/1941 | Leggiadro |
| 2,316,297 A | 4/1943 | Southerland |
| 2,840,070 A | 6/1958 | Tofflemire |
| 2,821,190 A | 1/1959 | Chase |
| 2,868,206 A | 1/1959 | Stoesser |
| 2,944,552 A | 7/1960 | Canon |
| 3,185,155 A | 5/1965 | Slaten |
| 3,224,320 A | 12/1965 | Knudsen |
| 3,297,022 A | 1/1967 | Wallace |
| 3,313,294 A | 4/1967 | Uddenberg |
| 3,336,916 A | 8/1967 | Edlich |
| 3,357,433 A | 12/1967 | Fourestier et al. |
| 3,568,677 A | 3/1971 | Nolan et al. |
| 3,613,682 A | 10/1971 | Naylor |
| 3,625,202 A | 12/1971 | Oyoshirhara |
| 3,805,793 A | 4/1974 | Wright |
| 3,835,841 A | 9/1974 | Terada |
| 3,856,016 A | 12/1974 | Davis |
| 3,857,386 A | 12/1974 | Ashbell |
| 3,866,601 A | 2/1975 | Russell |
| 3,882,854 A | 5/1975 | Hulka |
| 3,934,115 A | 1/1976 | Peterson |
| 3,980,861 A | 9/1976 | Fukunaga |
| RE29,088 E | 12/1976 | Shaw |
| 4,011,872 A | 3/1977 | Komiya |
| 4,031,898 A | 6/1977 | Hiltebrandt et al. |
| 4,038,987 A | 8/1977 | Komiya |
| 4,052,980 A | 10/1977 | Grams et al. |
| 4,132,227 A | 1/1979 | The |
| 4,175,545 A | 11/1979 | Termanini |
| 4,178,920 A | 12/1979 | Cawood et al. |
| 4,190,042 A | 2/1980 | Sinnreich |
| 4,196,734 A | 4/1980 | Harris |
| 4,232,660 A | 11/1980 | Coles |
| 4,257,420 A | 3/1981 | Terayama |
| 4,359,052 A | 11/1982 | Staub |
| 4,362,160 A | 12/1982 | Hiltebrandt |
| 4,369,768 A | 1/1983 | Vukovic |
| 4,372,295 A | 2/1983 | Heckele |
| 4,418,692 A | 12/1983 | Guay |
| 4,423,727 A | 1/1984 | Widran et al. |
| 4,428,746 A | 1/1984 | Mendez |
| 4,440,170 A | 4/1984 | Golden et al. |
| 4,493,321 A | 1/1985 | Leather |
| 4,493,711 A | 1/1985 | Chin et al. |
| 4,499,898 A | 2/1985 | Knepshield |
| 4,499,899 A | 2/1985 | Lyons, III |
| 4,516,574 A | 5/1985 | Hewes, Jr. |
| 4,516,575 A | 5/1985 | Gerhard et al. |
| 4,556,058 A | 12/1985 | Green |
| 4,557,255 A | 12/1985 | Goodman |
| 4,562,832 A | 1/1986 | Wilder et al. |
| 4,586,919 A | 5/1986 | Taheri |
| 4,587,968 A | 5/1986 | Price |
| 4,597,030 A | 6/1986 | Brody et al. |
| 4,597,389 A | 7/1986 | Ibrahim et al. |
| 4,600,940 A | 7/1986 | Sluyter |
| 4,607,622 A | 8/1986 | Fritch |
| 4,638,802 A | 1/1987 | Okada |
| 4,646,738 A | 3/1987 | Trott |
| 4,649,917 A | 3/1987 | Karasawa |
| 4,651,733 A | 3/1987 | Mobin-Uddin |
| 4,653,476 A | 3/1987 | Bonnet |
| 4,654,024 A | 3/1987 | Crittenden |
| 4,656,999 A | 4/1987 | Storz |
| 4,657,018 A | 4/1987 | Hakky |
| 4,662,068 A | 5/1987 | Polonsky |
| 4,667,655 A | 5/1987 | Ogiu et al. |
| 4,700,694 A | 10/1987 | Shishido |
| 4,702,246 A | 10/1987 | Ellis et al. |
| 4,726,370 A | 2/1988 | Karasawa et al. |
| 4,744,363 A | 5/1988 | Hasson |
| 4,745,908 A | 5/1988 | Wardle |
| 4,754,754 A | 7/1988 | Garito et al. |
| 4,759,348 A | 7/1988 | Cawood |
| 4,759,364 A | 7/1988 | Boebel |
| 4,762,120 A | 8/1988 | Hussein |
| 4,768,508 A | 9/1988 | Chin et al. |
| 4,772,093 A | 9/1988 | Abele et al. |
| 4,773,394 A | 9/1988 | Reichstein et al. |
| 4,779,611 A | 10/1988 | Grooters et al. |
| 4,793,346 A | 12/1988 | Mindich |
| 4,819,620 A | 4/1989 | Okutsu |
| 4,819,633 A | 4/1989 | Bauer et al. |
| 4,821,718 A | 4/1989 | Uldall |
| 4,838,246 A | 6/1989 | Hahn et al. |
| 4,858,595 A | 8/1989 | Buess et al. |
| 4,862,874 A | 9/1989 | Kellner |
| 4,865,019 A | 9/1989 | Phillips |
| 4,867,138 A | 9/1989 | Kubota et al. |
| 4,869,268 A | 9/1989 | Yoon |
| 4,874,375 A | 10/1989 | Ellison |
| 4,877,016 A | 10/1989 | Kantor et al. |
| 4,909,789 A | 3/1990 | Taguchi et al. |
| 4,919,129 A | 4/1990 | Weber, Jr. et al. |
| 4,924,851 A | 5/1990 | Ognier et al. |
| 4,924,882 A | 5/1990 | Donovan |
| 4,932,952 A | 6/1990 | Wojciechowicz, Jr. |
| 4,936,842 A | 6/1990 | D'Amelio et al. |
| 4,950,278 A | 8/1990 | Sachse et al. |
| 4,959,067 A | 9/1990 | Muller |
| 4,966,596 A | 10/1990 | Kuntz et al. |
| 4,985,030 A | 1/1991 | Melzer et al. |
| 4,991,565 A | 2/1991 | Takahashi et al. |
| 4,994,062 A | 2/1991 | Nishigaki et al. |
| 4,997,419 A | 3/1991 | Lakatos et al. |
| 4,997,436 A | 3/1991 | Oberlander |
| 4,998,527 A | 3/1991 | Meyer |
| 4,998,972 A | 3/1991 | Chin et al. |
| 5,007,907 A | 4/1991 | Nishigaki et al. |
| 5,007,908 A | 4/1991 | Rydell |
| 5,011,490 A | 4/1991 | Fischell et al. |
| 5,013,312 A | 5/1991 | Parins et al. |
| 5,020,514 A | 6/1991 | Heckele |
| 5,025,778 A | 6/1991 | Silverstein et al. |
| 5,026,370 A | 6/1991 | Lottick |
| 5,026,383 A | 6/1991 | Nobles |
| 5,035,232 A | 7/1991 | Lutze et al. |
| 5,037,433 A | 8/1991 | Wilk et al. |
| 5,047,038 A | 9/1991 | Peters et al. |
| 5,049,154 A | 9/1991 | Quadri |
| 5,053,041 A | 10/1991 | Ansari et al. |
| 5,100,420 A | 3/1992 | Green et al. |
| 5,171,311 A | 12/1992 | Rydell et al. |
| 5,181,919 A | 1/1993 | Bergman et al. |
| 5,188,630 A | 2/1993 | Christoudias |
| 5,190,541 A | 3/1993 | Abele et al. |
| 5,197,971 A | 3/1993 | Bonutti |
| 5,201,752 A | 4/1993 | Brown et al. |
| 5,213,093 A | 5/1993 | Swindle |
| 5,217,001 A | 6/1993 | Nakao et al. |
| 5,217,441 A | 6/1993 | Shichman |
| 5,230,621 A | 7/1993 | Jacoby |
| 5,251,613 A | 10/1993 | Adair |
| 5,258,006 A | 11/1993 | Rydell et al. |
| 5,259,366 A | 11/1993 | Reydel et al. |
| 5,269,753 A | 12/1993 | Wilk |
| 5,269,785 A | 12/1993 | Bonutti |
| 5,271,380 A | 12/1993 | Riek et al. |
| 5,271,385 A | 12/1993 | Bailey |
| 5,273,026 A | 12/1993 | Wilk |
| 5,275,608 A | 1/1994 | Forman et al. |

| Patent | Date | Name |
|---|---|---|
| 5,279,546 A | 1/1994 | Mische et al. |
| 5,284,128 A | 2/1994 | Hart |
| 5,284,478 A | 2/1994 | Nobles et al. |
| 5,290,284 A | 3/1994 | Adair |
| 5,300,036 A | 4/1994 | Mueller et al. |
| 5,312,423 A | 5/1994 | Rosenbluth et al. |
| 5,318,564 A | 6/1994 | Eggers |
| 5,318,586 A | 6/1994 | Ereren |
| 5,320,115 A | 6/1994 | Kenna |
| 5,322,503 A | 6/1994 | Desai |
| 5,334,150 A | 8/1994 | Kaali |
| 5,336,231 A | 8/1994 | Adair |
| 5,337,736 A | 8/1994 | Reddy |
| 5,339,803 A | 8/1994 | Mayzels et al. |
| 5,345,927 A | 9/1994 | Bonutti |
| 5,346,504 A | 9/1994 | Ortiz et al. |
| 5,352,219 A | 10/1994 | Reddy |
| 5,354,291 A | 10/1994 | Bales et al. |
| 5,359,995 A | 11/1994 | Sewell, Jr. |
| 5,366,476 A | 11/1994 | Noda |
| 5,368,015 A | 11/1994 | Wilk |
| 5,370,109 A | 12/1994 | Cuny |
| 5,373,840 A | 12/1994 | Knighton |
| 5,374,277 A | 12/1994 | Hassler |
| 5,376,076 A | 12/1994 | Kaali |
| 5,380,291 A | 1/1995 | Kaali |
| 5,383,889 A | 1/1995 | Warner et al. |
| 5,385,572 A | 1/1995 | Nobles et al. |
| 5,386,818 A | 2/1995 | Schneebaum et al. |
| 5,391,178 A | 2/1995 | Yapor |
| 5,395,367 A | 3/1995 | Wilk |
| 5,395,383 A | 3/1995 | Adams et al. |
| 5,397,335 A | 3/1995 | Gresal et al. |
| 5,403,312 A | 4/1995 | Yates et al. |
| 5,411,466 A | 5/1995 | Hess |
| 5,411,483 A | 5/1995 | Loomas et al. |
| 5,417,697 A | 5/1995 | Wilk et al. |
| 5,419,309 A | 5/1995 | Biehl |
| 5,423,813 A | 6/1995 | Kaiser et al. |
| 5,424,877 A | 6/1995 | Tsuyuki et al. |
| 5,425,355 A | 6/1995 | Kulick |
| 5,425,357 A | 6/1995 | Moll et al. |
| 5,431,151 A | 7/1995 | Riek et al. |
| 5,441,041 A | 8/1995 | Sauer et al. |
| 5,441,498 A | 8/1995 | Perkins |
| 5,447,513 A | 9/1995 | Davison et al. |
| 5,448,990 A | 9/1995 | De Faria-Correa |
| 5,450,842 A | 9/1995 | Tovey et al. |
| 5,452,732 A | 9/1995 | Bircoll |
| 5,460,629 A | 10/1995 | Shlain et al. |
| 5,468,248 A | 11/1995 | Chin et al. |
| 5,474,057 A | 12/1995 | Makower et al. |
| 5,486,155 A | 1/1996 | Muller et al. |
| 5,489,290 A | 2/1996 | Furnish |
| 5,490,836 A | 2/1996 | Desai |
| 5,496,317 A | 3/1996 | Goble et al. |
| 5,496,345 A | 3/1996 | Kieturakis et al. |
| 5,501,654 A | 3/1996 | Failla et al. |
| 5,505,686 A | 4/1996 | Willis et al. |
| 5,507,755 A | 4/1996 | Gresal et al. |
| 5,509,922 A | 4/1996 | Aranyi et al. |
| 5,511,564 A | 4/1996 | Wilk |
| 5,512,037 A | 4/1996 | Russell et al. |
| 5,514,151 A | 5/1996 | Fogarty et al. |
| 5,514,153 A | 5/1996 | Bonutti |
| 5,522,830 A | 6/1996 | Aranyi |
| 5,533,496 A | 7/1996 | De Faria-Correa et al. |
| 5,535,759 A | 7/1996 | Wilk |
| 5,536,251 A | 7/1996 | Evard et al. |
| 5,549,605 A | 8/1996 | Hahnen |
| 5,549,636 A | 8/1996 | Li |
| 5,549,637 A | 8/1996 | Crainich |
| 5,551,947 A | 9/1996 | Kaali |
| 5,554,101 A | 9/1996 | Matula et al. |
| 5,558,620 A | 9/1996 | Heckele et al. |
| 5,564,615 A | 10/1996 | Bishop et al. |
| 5,569,164 A | 10/1996 | Lurz |
| 5,569,183 A | 10/1996 | Kieturakis |
| 5,569,244 A | 10/1996 | Hahnen |
| 5,569,274 A | 10/1996 | Rapacki et al. |
| 5,569,291 A | 10/1996 | Privitera et al. |
| 5,571,100 A | 11/1996 | Goble et al. |
| 5,575,756 A | 11/1996 | Karasawa et al. |
| 5,588,581 A | 12/1996 | Conlon et al. |
| 5,591,183 A | 1/1997 | Chin |
| 5,599,349 A | 2/1997 | D'Amelio |
| 5,601,580 A | 2/1997 | Goldberg et al. |
| 5,601,581 A | 2/1997 | Fogarty et al. |
| 5,618,307 A | 4/1997 | Donlon et al. |
| 5,626,587 A | 5/1997 | Bishop et al. |
| 5,630,787 A | 5/1997 | Yabe et al. |
| 5,630,795 A | 5/1997 | Kuramoto et al. |
| 5,634,584 A | 6/1997 | Okorocha et al. |
| 5,634,924 A | 6/1997 | Turkel et al. |
| 5,653,722 A | 8/1997 | Kieturakis |
| 5,656,012 A | 8/1997 | Sienkiewicz |
| 5,658,282 A | 8/1997 | Daw et al. |
| 5,662,585 A | 9/1997 | Willis et al. |
| 5,662,588 A | 9/1997 | Iida |
| 5,662,662 A | 9/1997 | Bishop et al. |
| 5,665,096 A | 9/1997 | Yoon |
| 5,667,480 A | 9/1997 | Knight et al. |
| 5,669,906 A | 9/1997 | Grossi et al. |
| 5,673,840 A | 10/1997 | Schulze et al. |
| 5,680,982 A | 10/1997 | Schulze et al. |
| 5,683,349 A | 11/1997 | Makower et al. |
| 5,685,820 A | 11/1997 | Riek et al. |
| 5,688,269 A | 11/1997 | Newton et al. |
| 5,690,606 A | 11/1997 | Slotman |
| 5,695,448 A | 12/1997 | Kimura et al. |
| 5,700,236 A | 12/1997 | Sauer et al. |
| 5,702,408 A | 12/1997 | Wales et al. |
| 5,702,412 A | 12/1997 | Popov et al. |
| 5,704,372 A | 1/1998 | Moll |
| 5,704,534 A | 1/1998 | Huitema et al. |
| 5,707,389 A | 1/1998 | Louw et al. |
| 5,713,505 A | 2/1998 | Huitema |
| 5,716,352 A | 2/1998 | Viola et al. |
| 5,718,714 A | 2/1998 | Livneh |
| 5,720,761 A | 2/1998 | Kaali |
| 5,722,934 A | 3/1998 | Knight et al. |
| 5,725,479 A | 3/1998 | Knight et al. |
| 5,728,119 A | 3/1998 | Smith |
| 5,730,748 A | 3/1998 | Fogarty et al. |
| 5,738,628 A | 4/1998 | Sierocuk et al. |
| 5,743,880 A | 4/1998 | Hlavka |
| 5,749,870 A | 5/1998 | Gloth et al. |
| 5,752,966 A | 5/1998 | Chang |
| 5,759,150 A | 6/1998 | Konou et al. |
| 5,759,183 A | 6/1998 | VanDusseldorp |
| 5,759,188 A | 6/1998 | Yoon |
| 5,762,606 A | 6/1998 | Minnich |
| 5,766,169 A | 6/1998 | Fritzsch et al. |
| 5,766,215 A | 6/1998 | Muri et al. |
| 5,772,576 A | 6/1998 | Knighton et al. |
| 5,779,728 A | 7/1998 | Lunsford |
| 5,795,331 A | 8/1998 | Cragg et al. |
| 5,817,013 A | 10/1998 | Ginn et al. |
| 5,843,121 A | 12/1998 | Yoon |
| RE36,043 E | 1/1999 | Knighton |
| 5,857,961 A | 1/1999 | Vanden Hoek et al. |
| 5,871,496 A | 2/1999 | Ginn et al. |
| 5,895,352 A | 4/1999 | Kleiner |
| 5,895,353 A | 4/1999 | Lunsford |
| 5,897,487 A | 4/1999 | Ouchi |
| 5,908,429 A | 6/1999 | Yoon |
| 5,913,870 A | 6/1999 | DeFonzo et al. |
| 5,916,213 A | 6/1999 | Haissaguerre et al. |
| 5,921,993 A | 7/1999 | Yoon |
| 5,925,058 A | 7/1999 | Smith |
| 5,928,135 A | 7/1999 | Knight et al. |
| 5,928,138 A | 7/1999 | Knight et al. |
| 5,938,620 A | 8/1999 | Daxer |
| 5,957,923 A | 9/1999 | Hahnen et al. |
| 5,957,936 A | 9/1999 | Yoon et al. |
| 5,984,937 A | 11/1999 | Morse et al. |
| 5,984,938 A | 11/1999 | Yoon |
| 5,984,939 A | 11/1999 | Yoon |

| | | |
|---|---|---|
| 5,993,384 A | 11/1999 | Lunsford et al. |
| 6,036,713 A | 3/2000 | Kieturakis |
| 6,059,802 A | 5/2000 | Ginn |
| 6,071,232 A | 6/2000 | Knighton |
| 6,080,102 A | 6/2000 | Konou et al. |
| 6,099,534 A * | 8/2000 | Bates et al. .................. 606/127 |
| 6,120,434 A | 9/2000 | Kimura et al. |
| 6,123,689 A | 9/2000 | To |
| 6,129,661 A | 10/2000 | Iafrati et al. |
| 6,162,173 A | 12/2000 | Chin et al. |
| 6,176,825 B1 | 1/2001 | Chin et al. |
| 6,186,825 B1 | 2/2001 | Rogiel et al. |
| 6,234,958 B1 | 5/2001 | Snoke et al. |
| 6,277,137 B1 | 8/2001 | Chin |
| 6,312,442 B1 | 11/2001 | Kieturakis et al. |
| 6,348,037 B1 | 2/2002 | Chin et al. |
| 6,361,543 B1 | 3/2002 | Chin et al. |
| 6,387,043 B1 | 5/2002 | Yoon |
| 6,406,425 B1 | 6/2002 | Chin et al. |
| 6,520,975 B2 | 2/2003 | Branco |
| 6,558,313 B1 | 5/2003 | Knighton et al. |
| 6,562,051 B1 | 5/2003 | Bolduc |
| 6,648,898 B1 | 11/2003 | Baxter |
| 6,660,016 B2 | 12/2003 | Lindsay |
| 6,673,087 B1 | 1/2004 | Chang |
| 6,702,813 B1 | 3/2004 | Baxter et al. |
| 6,705,986 B2 | 3/2004 | Fiegel et al. |
| 6,730,020 B2 | 5/2004 | Peng et al. |
| 6,749,609 B1 | 6/2004 | Lunsford |
| 6,752,756 B2 | 6/2004 | Lunsford et al. |
| 6,762,368 B2 | 7/2004 | Saputro |
| 6,811,546 B1 | 11/2004 | Callas |
| 6,814,696 B1 | 11/2004 | Chang et al. |
| 6,814,743 B2 | 11/2004 | Chin |
| 6,830,546 B1 | 12/2004 | Chin et al. |
| 6,884,248 B2 | 4/2005 | Bolduc |
| 6,899,670 B2 | 5/2005 | Peng |
| 6,963,792 B1 | 11/2005 | Green |
| 6,972,028 B2 | 12/2005 | Chin |
| 6,976,957 B1 | 12/2005 | Chin et al. |
| 7,033,357 B2 | 4/2006 | Baxter et al. |
| 7,066,875 B2 | 6/2006 | Knighton et al. |
| 7,097,665 B2 | 8/2006 | Stack |
| 7,146,984 B2 | 12/2006 | Stack |
| 7,211,040 B2 | 5/2007 | Knighton et al. |
| 7,214,180 B2 | 5/2007 | Chin |
| 7,226,409 B2 | 6/2007 | Peng |
| 7,264,587 B2 | 9/2007 | Chin |
| 7,288,096 B2 | 10/2007 | Chin |
| 7,326,178 B1 | 2/2008 | Lunsford et al. |
| 7,344,536 B1 | 3/2008 | Lunsford |
| 7,364,657 B2 | 4/2008 | Mandrusov |
| 7,384,423 B1 | 6/2008 | Chin |
| 7,398,781 B1 | 7/2008 | Chin |
| 7,431,725 B2 | 10/2008 | Stack |
| 7,476,198 B1 | 1/2009 | Chin et al. |
| 7,479,104 B2 | 1/2009 | Lau |
| 7,485,092 B1 | 2/2009 | Stewart |
| 7,867,163 B2 | 1/2011 | Chin et al. |
| 7,972,265 B1 | 7/2011 | Chin et al. |
| 2002/0183593 A1 | 12/2002 | Chin et al. |
| 2003/0187460 A1 | 10/2003 | Chin |
| 2003/0187461 A1 | 10/2003 | Chin |
| 2003/0236544 A1 | 12/2003 | Lunsford |
| 2004/0097792 A1 | 5/2004 | Moll |
| 2004/0102804 A1 | 5/2004 | Chin |
| 2004/0153098 A1 | 8/2004 | Chin |
| 2004/0153101 A1 | 8/2004 | Bolduc |
| 2004/0181242 A1 | 9/2004 | Stack |
| 2004/0216748 A1 | 11/2004 | Chin |
| 2004/0236231 A1 | 11/2004 | Knighton |
| 2004/0236310 A1 | 11/2004 | Chin |
| 2005/0192613 A1 | 9/2005 | Lindsay |
| 2005/0247320 A1 | 11/2005 | Stack |
| 2005/0261712 A1 | 11/2005 | Balbierz |
| 2005/0266109 A1 | 12/2005 | Chin |
| 2005/0267499 A1 | 12/2005 | Stack |
| 2006/0052660 A1 | 3/2006 | Chin |
| 2006/0079915 A1 | 4/2006 | Chin |
| 2006/0116746 A1 | 6/2006 | Chin |
| 2006/0206121 A1 | 9/2006 | Chin |
| 2006/0270900 A1 | 11/2006 | Chin |
| 2006/0271032 A1 | 11/2006 | Chin |
| 2006/0287574 A1 | 12/2006 | Chin |
| 2006/0287734 A1 | 12/2006 | Stack |
| 2007/0060932 A1 | 3/2007 | Stack |
| 2007/0118206 A1 | 5/2007 | Colgan |
| 2007/0162067 A1 | 7/2007 | Lunsford |
| 2007/0198043 A1 | 8/2007 | Cox |
| 2007/0219571 A1 | 9/2007 | Balbierz |
| 2007/0238917 A1 | 10/2007 | Peng |
| 2007/0276432 A1 | 11/2007 | Stack |
| 2008/0039879 A1 | 2/2008 | Chin |
| 2008/0065122 A1 | 3/2008 | Stack |
| 2008/0097523 A1 | 4/2008 | Bolduc |
| 2008/0103365 A1 | 5/2008 | Chin |
| 2008/0132892 A1 | 6/2008 | Lunsford |
| 2008/0145345 A1 | 6/2008 | Mandrusov |
| 2008/0145469 A1 | 6/2008 | Chin |
| 2008/0306333 A1 | 12/2008 | Chin |
| 2008/0306335 A1 | 12/2008 | Lau |
| 2009/0024156 A1 | 1/2009 | Chin |

FOREIGN PATENT DOCUMENTS

| | | |
|---|---|---|
| AU | 1999-42354 | 7/1999 |
| AU | 199942354 A1 | 7/1999 |
| AU | 1999-035034 | 1/2000 |
| AU | 719712 | 8/2000 |
| AU | 2007-203086 | 7/2007 |
| CA | 2 244 164 | 1/1997 |
| CA | 2 274 270 | 12/1999 |
| CA | 2 279 661 | 2/2000 |
| CA | 2 592 766 | 6/2007 |
| DE | 24 15 263 A1 | 10/1975 |
| DE | 3525917 A1 | 2/1986 |
| DE | 3942589 A1 | 7/1991 |
| EP | 0 131 347 | 1/1985 |
| EP | 0 243 714 A2 | 11/1987 |
| EP | 0 341 943 | 11/1989 |
| EP | 0 664 104 | 7/1995 |
| EP | 0 681 811 A2 | 11/1995 |
| EP | 0 409 569 | 1/1997 |
| EP | 0 761 171 | 3/1997 |
| EP | 0 761 171 A2 | 3/1997 |
| EP | 0 761 171 B1 | 3/1997 |
| EP | 00769270 | 4/1997 |
| EP | 0 867 148 | 9/1998 |
| EP | 0 980 673 | 2/2000 |
| EP | 0 980 673 A2 | 2/2000 |
| FR | 2 265 344 | 10/1975 |
| GB | 2 082 459 | 3/1982 |
| GB | 2 195 540 | 4/1988 |
| JP | 7-27043 | 1/1995 |
| JP | 2802244 | 7/1998 |
| JP | 11-172954 | 6/1999 |
| JP | 11-225282 | 8/1999 |
| JP | 2000-037389 | 2/2000 |
| JP | 2007-509702 | 4/2007 |
| JP | 2007-175478 | 7/2007 |
| SU | 112367 | 6/1958 |
| SU | 510235 | 4/1976 |
| SU | 1371689 A1 | 2/1988 |
| WO | WO 91/08710 | 6/1991 |
| WO | WO 92/20291 | 11/1992 |
| WO | WO 94/18881 | 9/1994 |
| WO | WO 95/10982 | 4/1995 |
| WO | WO 95/19737 | 7/1995 |
| WO | WO 96/01130 | 1/1996 |
| WO | WO 96/30072 | 10/1996 |
| WO | WO 96/36287 | 11/1996 |
| WO | WO 97/16125 | 5/1997 |
| WO | WO 97/26831 | 7/1997 |
| WO | WO 97/33522 | 9/1997 |
| WO | WO 97/37701 | 10/1997 |
| WO | WO 98/02084 | 1/1998 |
| WO | WO 98/02102 | 1/1998 |
| WO | WO 98/06451 | 2/1998 |
| WO | WO 00/40139 | 7/2000 |

| WO | WO 00/40160 | 7/2000 |
| WO | WO 03/057062 A2 | 7/2003 |
| WO | WO 03/094758 A1 | 11/2003 |
| WO | WO 03/105706 | 12/2003 |
| WO | WO 2004/066828 A2 | 8/2004 |
| WO | WO 2004/066829 A2 | 8/2004 |
| WO | WO 2004/073506 | 9/2004 |
| WO | WO 2005/006955 A2 | 1/2005 |
| WO | WO 2005/044079 A2 | 5/2005 |

OTHER PUBLICATIONS

Memorandum re VasoView Feedback, Aug. 29, 1996.
Memorandum re VasoView Continued Release Plan, Dec. 11, 1996.
VasoView 2 Thoughts by Scott C. Anderson, Oct. 10, 1996.
Excerpt from Frazier Lab Notebook No. 144, Jun. 9, 1997.
Excerpt from Frazier Lab Notebook No. 152, Jun. 9, 1997.
Orbital Dissection Cannula Product Specification, Jun. 7, 1997.
Attachment A PPAQ Approval, Design Review, Design Freeze, Apr. 15, 1997.
VasoView Oribital Dissector Dissection Cannula IFU, Mar. 14, 1997.
Senior Staff update, May 5, 1997.
Disengagement project Scope for Enhanced Orbital Dissector, Dec. 18, 1997.
Excerpt from Frazier Lab Notebook No. 144, Nov. 3, 1997.
Excerpt from Tachi Callas Lab notebook No. 152, Nov. 3, 1997.
Orbital Dissection Cannula Enhanced Version Product Specification, Nov. 4, 1997.
Attachment A PPAQ Approval, Design Review, Design Freeze, Sep. 15, 1997.
Attachment A, Nov. 4, 1997.
McCoy Lab Notebook No. 166, Sep. 5, 1997.
VasoView III Development Team Market Preference Data Sheet, Sep. 4, 1997.
VasoView Big Balloon & Handle Market Preference Data Sheet, Mar. 11, 1997.
Product Specification History Dissection Tools, Jun. 27, 1996.
Product Specification for VasoView Dissection Tools (Rev date Apr. 15, 1996).
Memo to file re Monthly Program Review Summaries, Jul. 9, 1996.
Memo to Total Heart Team regarding Notes from Assn of PA Annual meeting, Jan. 26, 1996.
Memo re FMEA Rationale for SVH Balloon Dissection Cannula, Jun. 24, 1996.
Memo regarding Design Review Path Freeze Criteria OMS-BDS, Jul. 1, 1996.
Product Specification VasoView Balloon Dissection System, Jun. 21, 1996.
VasoView Balloon Dissection System Design Validation Conclusions, Jul. 10, 1996.
VasoView Balloon Dissection System Market Preference Data Sheet, Jul. 2, 1996.
Email regarding Pig Lab Results, Aug. 4, 1995.
Summary of Clinical, Jul. 3, 1996.
VasoView Balloon Dissection System Market Preference Data Sheet, May 29, 1996.
Chin Letter to FDA regarding Pre-Market notification 510K for Tapered Tip Balloon Dissection Cannula, Jul. 17, 1995.
VasoView Balloon Dissection System Market Release Meeting, Jul. 11, 1996.
VVII Team Meeting, Dec. 4, 1996.
Jeffrey Wayne Baxter deposition transcript, Sep. 26, 2008.
Albert Chin deposition transcript, Sep. 10, 2008.
Edwin Hlavka deposition transcript, Sep. 8, 2008.
John Lunsford deposition transcript, Sep. 24, 2008.
Justin Williams deposition transcript, Oct. 8, 2008.
Eric Willis deposition transcript, Oct. 7, 2008.
Responses of Maquet Cardiovascular, L.L.C. to Respondents Terumo Corporation and Terumo Cardiovascular Systems Corporation's Second Set of Requests for Admission, Nov. 3, 2008.
Supplemental Responses of Maquet Cardiovascular, L.L.C. to Respondents Terumo Corporation and Terumo Cardiovascular Systems Corporation's Requests for Admission Nos. 8-56, Nov. 20, 2008.
Responses of Maquet Cardiovascular, L.L.C. to Respondents Terumo Corporation and Terumo Cardiovascular Systems Corporation's Third Set of Request for Admission, Nov. 24, 2008.
Responses of Maquet Cardiovascular L.L.C. to Certain Interrogatories from Respondents Terumo Corporation and Terumo Cardiovascular Systems Corporation's First Set of Interrogatories [Nos. 3, 5, 7, 12, 23, 45, 48, 49, 59, 62, and 69], May 23, 2008.
Responses of Maquet Cardiovascular L.L.C. to Respondents Terumo Corporation and Terumo Cardiovascular Systems Corporation's First Set of Interrogatories [Nos. 1-78], Jun. 6, 2008.
Supplemental Responses of Maquet Cardivasular L.L.C. to Respondents Terumo Corporation and Terumo Cardiovascular Systems Corporation's Interrogatory Nos. [5, 6, 8, 14, 32, 33 & 67], Jul. 23, 2008.
Supplemental Responses of Maquet Cardiovascular L.L.C. to Respondents Terumo Corporation and Terumo Cardiovascular Systems Corporation's Interrogatory No. 21, Sep. 5, 2008.
Responses of Maquet Cardiovascular L.L.C. to Respondents Terumo Corporation and Terumo Cardiovascular Systems Corporation's Systems Corporation's Third Set of Interrogatories [Nos. 87-115], Aug. 6, 2008.
Responses of Maquet Cardiovascular L.L.C. To Respondents Terumo Corporation and Terumo Cardiovascular Systems Corporation's Fourth Set of Interrogatories [Nos. 116-148], Aug. 11, 2008.
Supplemental Responses of Maquet Cardiovascular L.L.C. to Respondents Terumo Corporation and Terumo Cardiovascular Systems Corporation's Fourth Set of Interrogatories, Sep. 12, 2008.
Second Supplemental Responses of Maquet Cardiovascular L.L.C. To Respondents Terumo Corporation and Terumo Cardiovascular Systems Corporation's Interrogatory Nos. 130, 131, 133, 134, 136 & 137, Oct. 21, 2008.
Supplemental Response of Maquet Cardiovascular L.L.C. to Respondents Terumo Corporation and Terumo Cardiovascular Systems Corporation's Interrogatory Nos. 146 & 148, Oct. 31, 2008.
Responses of Maquet Cardiovascular L.L.C. to Respondents Terumo Corporation and Terumo Cardiovascular Systems Corporation's Fifth Set of Interrogatories [Nos. 149-152], Sep. 5, 2008.
Responses of Maquet Cardiovascular L.L.C. to Respondents Terumo Corporation and Terumo Cardiovascular Systems Corporation's Sixth Set of Interrogatories [Nos. 153-155], Sep. 10, 2008.
Responses of Maquet Cardiovascular L.L.C. to Respondents Terumo Corporation and Terumo Cardiovascular Systems Corporation's Seventh Set of Interrogatories, Nov. 21, 2008.
Responses of Maquet Cardiovascular L.L.C. to Respondents Terumo Corporation and Terumo Cardiovascular Systems Corporation's Eighth Set of Interrogatories, Nov. 24, 2008.
U.S. Appl. No. 60/148,130, filed Aug. 10, 1999, Chin.
U.S. Appl. No. 60/150,737, filed Aug. 25, 1999, Chin.
U.S. Appl. No. 08/269,666, filed Jul. 1, 1994, Chin.
U.S. Appl. No. 08/502,494, filed Mar. 14, 2000, Chin et al.
U.S. Appl. No. 08/593,533, filed Jan. 24, 1996, Chin.
U.S. Appl. No. 09/133,136, filed Aug. 12, 1998, Chin.
U.S. Appl. No. 09/227,393, filed Jan. 8, 1999, Lunsford et al.
U.S. Appl. No. 09/413,012, filed Oct. 5, 1999, Chin et al.
U.S. Appl. No. 09/635,721, filed Aug. 9, 2000, Chin.
U.S. Appl. No. 09/738,608, filed Dec. 14, 2000, Chin.
U.S. Appl. No. 09/739,595, filed Dec. 15, 2000, Chang.
U.S. Appl. No. 09/750,848, filed Dec. 27, 2000, Chin.
U.S. Appl. No. 10/345,666, filed Jan. 16, 2003, Stack.
U.S. Appl. No. 10/371,537, filed Feb. 21, 2003, Beavers.
U.S. Appl. No. 11/962,517, filed Dec. 21, 2007, Chin.
U.S. Appl. No. 90/004/4.301, filed Jul. 12, 1996, Knighton et al.
MacKenzie, The Use of Laryngoscope in Diseases of the Throat: with an essay on Hoarseness Loss of Voice, and Stridulous Breathing, In Relation to Nervo-Muscular Affection of the Larynx (1869).
Schwyzer, "On Bronchoscopy. With Report of a Case in Which a Foreign Body was Removed from the Right Lower Lobe of a Lung Through a Bronchoscope", Read before the Minnesota Academy of Medicine pp. 194-206 (Dec. 2, 1903).
Mathews, A Treatise on Diseases of the Rectum, Anus, and Signoid Flexure (1903).
Mayo, "The Surgical Treatment of Varicose Veins", The St. Paul Medical Journal, vol. VI, pp. 695-699 (1904).

Fenwick, "A Handbook of Clinical Electric-Light Cystoscopy" (1905).

Carrel et al.., "Uniterminal and Biterminal Venous Transplantations", Surgery, Gynecology and Obstetrics, vol. II, pp. 266-286 (1906).

Mayo, "Treatment of Varicose Veins", Surgery, Gynecology and Obstetrics, pp. 385-388 (1906).

Carrel et al., "Results of the Biterminal Transplantation of Veins", pp. 415-422 (1906).

Jackson, "Endothelioma of the Right Bronchus Removed by Peroral Bronchoscopy", The American Journal of the Medical Sciences, vol. CLIII, pp. 37-375 (1917).

Stern, "Resection of Obstruction at the Vesical Orifice; New Instruments Resectotherm; Resectoscope and New Method", Journal of American Medical Association, vol. 87, No. 21, pp. 1726-1730 (1926).

Chandler, "Internal Pneumolysis: Results of 110 Consecutive Operations", The Lancet, pp. 879-882 (Oct. 19, 1935).

Hurley, "Some Practical Guiding Principles for Closed Pneumonolysis", Canad. M.A.J., vol. 56, pp. 625-627 (Jun. 1947).

Bayliss, "Closed Intrapleural Pneumonolysis", Chest, vol. XIII, pp. 479-515 (1947).

Sarot et al., "Closed Pneumonolysis (Enucleation Technique)", Chest, vol. XVI, No. 5, pp. 509-542 (Nov. 1949).

Morris et al., "Arterial Bypass Below the Knee", Surgery, Gynecology & Obstetrics, vol. 108, pp. 321-332 (Jan.-Jun. 1959).

Hall, "The Great Saphenous Vein Used in Situ as an Arterial Shunt After Extirpation of the Vein Valves", Surgery, vol. 51. No. 4, pp. 492-495 (Apr. 1962).

Linton et al., "Autogenous Saphenous Vein Bypass Grafts in Femoropopliteal Obliterative Arterial Disease", Surgery, vol. 51, No. 1. pp. 62-73 (Jan.-Jun. 1962).

Palva, "Mediastinoscopy—A New Field for Bronchologists", Acta Oto-Laryngologica, vol. 53, Issue 2 & 3 (1961), http://www.informaworld.com/smpp/content.

Lore, "Tender Grip Forceps", The American Journal of Surgery, vol. 104, pp. 84-85 (Jul. 1962).

May et al., "Arterialized In Situ Saphenous Vein", Archives of Surgery, vol. 91, No. 5, pp. 743-750 (Nov. 1965).

Steptoe, "Abdominal Laparoscopy", Laparoscopy in Gynaecology, pp. 13-25 (1967).

Favaloro, "Saphenous Vein Graft in the Surgical Treatment of Coronary Artery Disease", The Journal of Thoracic and Cardiovascular Surgery, vol. 58. No. 2, (Aug. 1969).

Samuels et al., "In Situ Saphenous Vein Arterial Bypass: A Study of the Anatomy Pertinent to its Use in Situ as a Bypass Graft with a Description of a New Venous Valvulatome", The American Surgeon, vol. 34, No. 2, pp. 122-130 (February.

Barner et al., "Late Failure of Arterialized in Situ Saphenous Vein", Archives of Surgery, vol. 99, pp. 781-786 (Dec. 1969).

Effler et al., "The Simple Approach to Direct Coronary Artery Surgery", The Journal of Thoracic and Cardiovascular Surgery, vol. 62, No. 4, pp. 503-510 (Oct. 1971).

Nagovitsyn, "Varicocide Treatment of Varicose Veins of the Lower Extremities" (1971).

Koontz et al., "Factors Influencing Patency of the Autogenous Vein-Femoropoliteal Bypass Grafts: An Analysis of 74 Cases". Surgery, vol. 71. No. 5, pp. 753-759 (May 1972).

Rizk et al., "Vascular Endoscopy", Radiology, vol. 106, No. 1, pp. 33-35 (Jan. 1973).

Balasegaram, "Hepatic Surgery: A Review of a Personal Series of 95 Major Resections", The Australian and New Zealand Journal of Surgery, vol. 42. No. 1, pp. 1-10 (Aug. 1972).

Brody et al., "Changes in Vein Grafts Following Aorto-Coronary Bypass Induced by Pressure and Ischemia", The Journal of Thoracic and Cardiovascular Surgery, vol. 64. No. 6, pp. 847-854 (Dec. 1972).

Jones et al., "Lesions Observed in Arterial Autogenous Vein Grafts", Cardiovascular Surgery, pp. 198-210 (1972).

Kern et al., "The Intimal Proliferation in Aortic-Coronary Saphenous Vein Grafts: Light and electron microscopic studies", American Heart Journal, pp. 771-777 (Dec. 1972).

Crispin et al., "Intravascular Observation and Surgery Using the Flexible Fibrescope", The Lancet, pp. 750-751 (Apr. 7, 1973).

Abbott et al., "Structural Changes During Preparation of Autogenous Venous Grafts", Surgery, vol. 76, No. 6, pp. 1031-1040 (Dec. 1974).

Brook, "A historical review of the histology of patent autogenous vein grafts and vein patches", The Journal of Cardiovascular Surgery, vol. 16. No. 1, pp. 43-52 (Jan.-Feb. 1975).

Shepherd et al., "Physical Characteristics of Venous System in Man", Veins and their Control, pp. 171-172 (1975).

Cutler et al., "Autologous Saphenous vein femoropopliteal bypass: Analysis of 298 cases", Surgery, vol. 79, No. 3, pp. 325-331 (Mar. 1976).

Lukomsky et al., "Diagnosing Phasic Nature of Pulmonary Carcinoma by Means of Combined Mediastino-Laparoscopy" 1976.

Corson, "Chapter 10: Operating Room Preparation and Basic Techniques", Laparoscopy, pp. 88-102 (1977).

Gottlob, "The preservation of the venous endothelium by <<dissection without touching>> and by an atraumatic technique of vascular anastomosis". Minerva Chirurgica, vol. 32, pp. 693-700 (1977).

Tarlovskaya et al., "Endoscopic Investigations for Determining Lung Cancer Stage" (1978).

Stiles, "Technique of Saphenous vein aorta-coronary bypass grafting", The Journal of Thoracic and Cardiovascular Sugery, vol. 78, No. 2, pp. 305-308 (Aug. 1979).

May et al., "Concluding Remarks on the Therapy of Incompetent Perforating Veins", Perforating Veins, pp. 251-253 (1981).

Szilagyi et al., "Autogenous vein grafting in femoropopliteal atherosclerosis:The limits of its effectiveness", Surgery, vol. 86, No. 6, pp. 836-851 (1979).

Flemma et al., "Complications of Aortocoronary Bypass Grafting", Complications of Intrathoracic Surgery, pp. 167-177 (1979).

Ochsner et al., "The Internal Mammary Artery as a Coronary Artery Bypass Graft", Coronary Heart Surgery, pp. 120-124 (1979).

Buxton et al., "The significance of vein wall thickness and diameter in relation to the patency of femoropopliteal Saphenous vein bypass grafts", Surgery, vol. 87, No. 4, pp. 425-431 (Apr. 1980).

Hofer et al., "Morphologic Studies in Saphenous Vein Grafts for Aorto-coronary Bypass Surgery Part 1: Morphology of the Graft Using Ordinary Surgical Preparation Techniques", The Thoracic and Cardiovascular Surgeon, vol. 29, No. 1, pp. 32-37 (1981).

Bonchek, "Prevention of endothelial damage during preparation of Saphenous veins for bypass grafting", The Journal of Thoracic and Cardiovascular Surgery, vol. 79, No. 6. pp. 911-915 (Jun. 1980).

McGeachie et al.. "Vein to Artery Grafts: A Quantitative Study of Revascularization by Vasa Vasorum and its Relationship to Intimal Hyperplasia". Annals of Surgery, vol. 194. No. 1, pp. 100-107 (Jul. 1981).

Gundry et al., "Intraoperative Trauma to Human Saphenous Veins: Scanning Electron Microscopic Comparison of Preparation Technictues". The Annals of Thoracic Surgery, vol. 30. No. 1, pp. 40-47 (Jul. 1980).

Buchbinder et al., "Comparison of Patency Rate and Structural Change in In Situ and Reversed Vein Arterial Bypass", Journal of Surgical Research, vol. 30. No. 3, pp. 213-222 (Mar. 1981).

Gundry et al., "Optimal preparation techniques for human Saphenous vein grafts", Surgery, vol. 88, No. 6, pp. 785-794 (Dec. 1980).

Moser, "Angioscopic Visualization of Pulmonary Emboli", Chest, vol. 77, No. 2, pp. 198-201 (Feb. 1980).

Ford et al., "Isolation of Adult Canine Venous Endothelium for Tissue Culture", In Vitro, vol. 17, No. 1, pp. 44-50 (Jan. 1980).

DeLaria et al., "Leg wound complications associated with coronary revascularization", The Journal of Thoracic and Cardiovascular Surgery, vol. 81, pp. 403-407 (1981).

Fogarty et al.., "Adjunctive Intraoperative Arterial Dilation: Simplified Instrumentation Technique", Archives of Surgery, vol. 116, No. 11, pp. 1391-1398 (Nov. 1981).

Logerfo et al., "An improved technique for preservation endothelial morphology in vein grafts", Surgery, vol. 90, No. 6, pp. 1015-1024 (Dec. 1981).

Greenberg et al., "Vein-Donor-Leg Cellulities After Coronary Artery Bypass Surgery", Annals of Internal Medicine, vol. 97, No. 4, pp. 565-566 (Oct. 1982).

Gunstensen et al., "Intimal Hyperplasia in Autogenous Veins Used for Arterial Replacement", The Canadian Journal of Surgery, vol. 25. No. 2. pp. 158-165 (Mar. 1982).

McGoon, "Incision Decision Advertisement", The Journal of Thoracic and Cardiovascular Surgery, vol. 83, No. 5 (May 1982).
Catinella et al.., "The factors influencing early patency of coronary artery bypass vein grafts: Correlation of angiographic and ultrastructure findings", The Journal of Thoracic Cardiovascular Surgery, vol. 83, No. 5, pp. 686-700 (May 1982).
Feikes et al., "Harvesting and protection of the Saphenous vein associated with early delivery of blood cardioplegia in coronary artery bypass graft surgery", American Heart Journal. vol. 104. No. 2. Part 1, pp. 329-332 (1982).
Leather et al., "The In Situ Saphenous Vein for Arterial Bypass", Biologic and Synthetic Vascular Prostheses, pp. 351-364 (1982).
Sottiurai et al., "Autogenous Vein Grafts: Experimental Studies", Biologic and Synthetic Vascular Prostheses, pp. 311-364 (1982).
Kinney et al., "Transluminal Angioplasty: A Mechanical-Pathophysiological Correlation of its Physical Mechanisms", Radiology, vol. 153, No. 1, pp. 85-89 (Oct. 1984).
Teimourian et al., "Subcutaneous Endoscopy in Suction Lipectomy", Plastic and Reconstructive Surgery, vol. 74, No. 5, pp. 708-711 (Nov. 1984).
Gregory et al., "Composite Grafts: An Alternative to Saphenous Vein for Lower Extremity Arterial Reconstruction", The Journal of Cardiovascular Surgery vol. 24. No. 1. pp. 53-57 (Jan.-Feb. 1983).
Hufnagel, "Chapter 1: History of Vascular Grafting", Vascular Grafting—Clinical Appliations and Techniques, pp. 1-12 (1983).
Shah et al., "In Situ Saphenous Vein Arterial Bypass", Vascular Grafting: Clinical Applications and Techniques, pp. 133-147 (1983).
Baddour et al., "Recurrent Cellulitis After Coronary Bypass Surgery", The Journal of the American Medical Journal, vol. 251. No. 8, pp. 1049-1052 (Feb. 17, 1984).
Chin et al., "A Physical Measurement of the Mechanisms of Transluminal Angioplasty", Surgery, vol. 95, No. 2, pp. 196-201 (Feb. 1984).
Crew et al., "Carotid Surgery without Angiography", The American Journal of Surgery, vol. 148, pp. 217-220 (Aug. 1984).
Adcock et al., "Optimal Techniques for Harvesting and Preparation of Reversed Autogenous Vein Grafts for Use as Arterial Substitutes: A Review", vol. 96. No. 5. (Nov. 1984).
Rashid et al., "Subcutaneous Technique for Saphenous Vein Harvest", The Annals of Thoracic Surgery, vol. 37, No. 2, pp. 169-170 (Feb. 1984).
Ben-Simhon et al., "Vein Harvesting by Long Blunt and Blind Dissection. A Standardized Technique in the Dog", Biomaterials, Medical Devices, and Artificial Organs, vol. 12, No. 1 & 2, pp. 51-66 (1984).
Dorsey, "Harvesting the Greater Saphenous Vein with a Subcutaneous Vein Remover", The Canadian Journal of Surgery, vol. 28, No. 1, pp. 13-14 (Jan. 1985).
Tilanus et al., "Saphenous Vein or PTFE for Femoropopliteal Bypass", Annals of Surgery, vol. 202, No. 6, pp. 780-782 (Dec. 1985).
Dorsey, "Saphenous Vein Harvesting Using a Subcutaneous Vein Remover", Minnesota Medical Association, pp. 195-198 (Mar. 1985).
Baddour, "Delayed Soft Tissue Infections in Saphenous Venectomy Limbs of Coronary Bypass Patients", Infections in Surgery, vol. 4, No. 4, pp. 243-248 (Apr. 1985).
Spears et al., "Coronary Angioscopy During Cardiac Catheterization", Journal of the American College of Cardiology, vol. 6, No. 1, pp. 93-97 (Jul. 1985).
Hulka et al., "Standard Gynecologic Techniques", Textbook of Laparoscopy, (1994).
Hobbs, "A New Approach to Short Saphenous Vein Varicosities", Surgery of Veins, pp. 301-321 (1985).
Nagovitsyn, "Operative Treatment of Acute Thrombophlebitis of the Superficial Veins of the Lower Extremities" (1985).
Weaver et al., "The Lesser Saphenous Vein: Autogenous Tissue for Lower Extremity Revascularization", Journal of Vascular Surgery, vol. 5. No. 5, pp. 687-692 (May 1987).
Scher et al., "Prevention and Management of Ischemic Complications of Vein Harvest Incisions in Cardiac Surgery Case Reports", Angiology. The Journal of Vascular Diseases. vol. 37. No. 1, pp. 119-123 (Jan. 1986).

Taylor et al., "Present Status of Reversed Vein Bypass for Lower Extremity", Journal of Vascular Surgery, vol. 3, No. 2, pp. 288-297 (Feb. 1986).
Meldrum-Hanna, "Long Saphenous Vein Harvesting", The Australian and New Zealand Journal of Surgery, vol. 56, No. 12, pp. 923-924 (Dec. 1986).
Raess et al., "Lesser Saphenous Vein as an Alternative Conduit of Choice in Coronary Bypass Operations", The Annals of Thoracic Surgery, vol. 41, No. 3, pp. 334-336 (Mar. 1986).
Sanborn, "Vascular Endoscopy: Current State of the Art", British Medical Bulletin, vol. 42, No. 3, pp. 270-273 (Apr. 1986).
Grundfest et al., "The Current Status of Angioscopy and Laser Angioplasty", Journal of Vascular Surgery, vol. 5, No. 4, pp. 667-673 (Apr. 1987).
LeMaitre et al., "In Situ Grafting Made Easy", Archives of Surgery, vol. 123, No. 1, pp. 101-103 (Jan. 1988).
Fleisher et al., "Angioscopically Monitored Saphenous Vein Valvulotomy", Journal of Vascular Surgery, vol. 4, No. 4, pp. 360-364 (Oct. 1986).
Miller, "Endoscopic Surgery of the Upper Urinary Tract", British Medical Bulletin, vol. 43, No. 3, pp. 274-279 (1986).
Nagovitsyn, "The Endoscopic Correction of the Shin Venous Blood Flow", Vestnik Khriurgii, vol. 137, No. 11, pp. 48-51 (Nov. 1986).
Noera et al., "Microscopic Evaluation in Saphenous Veins Used as Aortocoronary Bypass Grafts", Giornale Italiano di Cardiologia, vol. 16, No. 12, pp. 1037-1042 (Dec. 1986).
Suma et al. "Vein Perfusions System" for Harvesting the Saphenous Vein Graft in Coronary Bypass Surgery, Kyobu Geka, vol. 39, No. 8, pp. 622-623 (Aug. 1986).
Mehigan, "Symposium:Vascular Application of Angioscopy and Lasers", Journal of Vascular Surgery, vol. 5, No. 4, pp. 664-666 (Apr. 1987).
Taylor et al., "Autogenous Reversed Vein Bypass for Lower Extremity Ischemia in Patients with Absent of Inadequate Greater Saphenous Vein", The American Journal of Surgery, vol. 153, pp. 505-510 (May 1987).
Hashizume et al., "Intimal Response of Saphenous Vein to Intraluminal Trauma by Simulated Angioscope Insertion", Journal of Vascular Surgery, vol. 5. No. 6, pp. 862-868 (Jun. 1987).
Spyt, "Harvesting of the Lesser Saphenous Vein", The Annals of Thoracic Surgery, vol. 43, No. 6, p. 691 (Jun. 1987).
White, "Angioscopy and Laser in cardiovascular Surgery: Current Applications and Future Prospects", Aust. N. Z. J. Surg., vol. 58. No. 271-274 (1988).
Matsumoto et al., "Direct Vision Valvulotomy in In Situ Venous Bypass", Surgery Gynecology & Obstetrics, vol. 165, No. 4 (Oct. 1987).
Classen et al., "Electronic Endoscopy—The Latest Technology", Endoscopy, vol. 19, pp. 118-123 (1987).
Delmotte, "The Electronic Video Endoscope of Tomorrow, but First, its Present Status", Acta Endoscopica, vol. 17, No. 2, No. 89-91 (1987).
Dimitri et al., "A Quick and Atraumatic Method of Autologous Vein Harvesting Using the Subcutaneous Extraluminal Dissector". The Journal of Cardiovascular Surgery, vol. 28. No. 2, pp. 103-111 (Mar.-Apr. 1987).
Secroun, "Future Methods of Endoscopy", Acta Endoscopica, vol. 17, No. 2, pp. 92-95 (1987).
Lannerstad et al., "Effects of Different Graft Preparation Techniques on the Acute Thrombogenicity of Autologous Vein Grafts", European Surgical Research, vol. 19, pp. 395-399 (Nov.-Dec. 1987).
Towne, "Vascular Endoscopy", Perioperative Assessment in Vascular Surgery, pp. 303-313 (1987).
Chin et al., "The Effect of Valvulotomy on the Flow Rate Through the Saphenous Vein Graft: Clinical Implications", Journal of Vascular Surgery, vol. 8, No. 3, pp. 316-320 (Sep. 1988).
Wood, "Locating Previously "Stripped" Venous Systems and Harvesting of Lesser Saphenous Vein", The Annals of Thoracic Surgery, vol. 45, No. 3 (Mar. 1988).
Takemoto, "Electronic Endoscopy: Its Present and Future", Journal of Gastroenterology and Hepatology, vol. 4, pp. 75-80 (1989).

Cardella et al., "Lower-Extremity Venous Thrombosis: Comparison of Venography, Impedance Plethysmography, and Intravenous Manometry". Radiology. vol. 168, No. 1 , pp. 109-112 (Jul. 1988).
Citrin et al., "Replacement of the Carotid Artery Using Nonreversed Saphenous Vein", Surgery, Gynecology & Obstetrics. vol. 167, pp. 155-157 (Aug. 1988).
Woelfle et al., "Intraoperative Assessment of In Situ Saphenous Vein Bypass Grafts by Vascular Endoscopy", European Journal Vascular Endovascular Surgery European. vol. 2, pp. 257-262 (Aug. 1988).
Patel et al., "The Use of Fiber-Optic Intraluminal Transillumination for Saphenous Vein Harvesting", Journal of Vascular Surgery. vol. 8. No. 3, pp. 346-348 (Sep. 1988).
Gaudiani et al., "An Improved Technique for the Internal Mammary Artery Coronary Bypass Graft Procedure", Journal of Cardiac Surgery, vol. 3. No. 4. pp. 467-473 (Dec. 1988).
Hauer et al., "Endoscopic Subfascial Dissection of Perforating Veins", Surgical Endoscopy, vol. 2, pp. 5-12 (1988).
Lee et al., "Hazards of Angioscopic Examination: Documentation of Damage to the Arterial Intima", American Heart Journal. vol. 116, No. 6. pp. 1530-1536 (Dec. 1988).
Rey et al., "Electronic Video Endoscopy: Preliminary Results of Imaging Modification", Endoscopy, vol. 20, pp. 8-10 (1988).
Taylor et al., "Reversed vs. In Situ: Is Either the Technique of Choice for Lower Extremity Vein Bypass?", Perspectives in Vascular Surgery, vol. 1, No. 1, pp. 35-59 (1988).
Barnes et al., "Technical Innovations in Nonreversed Translocated Saphenous Vein Bypass", Journal of Vascular Surgery, vol. 9, No. 3, pp. 499-501 (Mar. 1989).
Chin et al., "Technique Using the Fiberoptic Valvulotome for the In Situ Vein Graft", Surgery Gynecology & Obstetrics, vol. 169, No. 3, pp. 255-256 (Sep. 1989).
Hauer, "Diagnosis and surgical management of varicosities", Herz, vol. 14, No. 5, pp. 274-282 (1989).
Fogarty et al., "Combined Thrombectomy and Dilation for the Treatment of Acute Lower Extremity Arterial Thrombosis", Journal of Vascular Surgery, vol. 10, No. 5, pp. 531-534 (Nov. 1989).
Burnand, "Reversed Saphenous Vein for Femoropopliteal Bypass Grafting", Vascular Surgical Techniques An Atlas, pp. 228-234 (1989).
Chin et al., "Angioscopic Preparation for Saphenous Vein In Situ Bypass Grafting", Endovascular Surgery, pp. 74-81 (1989).
Lavee et al., "Complications of Saphenous Vein Harvesting Following Coronary Artery Bypass Surgery", The Journal of Cardiovascular Surgery, vol. 30, No. 6, pp. 989-991 (1989).
Utley et al., "Preoperative Correlates of Impaired Wound Healing After Saphenous Vein Excision", The Journal of Cardiovascular Surgery, vol. 98. No. 1, pp. 147-149 (1989).
Veith et al., Short Vein Grafts in Limb-saving Arterial Reconstructions, Journal of Vascular and Interventional Radiology, vol. 1, No. 1, pp. 57-61 (Nov. 1990).
Louagie et al., "Viability of Long-Term Cryopreserved Human Saphenous Vein", The Journal of Cardiovascular Surgery, vol. 31. No. 1. pp. 92-100 (Jan.-Feb. 1990).
Galloway, JR. et al., "A new Device for Interactive, Image- Guided Surgery", Medical Imaging V: Image Capture, Formatting, and Display. SPIE-The International Society of Optical Engineering (Feb. 1991).
Myers et. al., "Semi-closed, ex-situ, non-reversed or reversed autogenous vein grafting", The Journal of Cardiovascular surgery, vol. 32. No. 1, pp. 110-116 (Jan.-Feb. 1991).
Bailey et al., "Laparoscopic Cholecystectomy: Experience with 375 Consecutive Patients", Ann. Surg., vol. 214, No. 4, pp. 531-540 (1991).
The Southern Surgeons Club, "A Prospective Analysis of 1518 Laparoscopic Cholecystectomies", New England Journal of Medicine, vol. 324, pp. 1073-1078 (Apr. 18, 1991).
Clayman et al.., "Laparoscopic Nephrectomy", The New England Journal of Medicine, vol. 324, No. 19, pp. 1370-1371 (May 9, 1991).
Lam, et al., "Surgical Procedures for Uncomplicated ("Routine") Female Stress Incontinence", The Urologic Clinics of North America. vol. 18. No. 2, pp. 327-337 (May 1991).
Couto et al., "Endoscopic ligation of perforator leg veins", The Lancet, vol. 337, p. 1480 (Jun. 15, 1991).

Milgalter et al., "A technique to harvest the inferior epigastric arteries for coronary bypass procedures", Journal of Cardiac Surgery, vol. 6, No. 2, pp. 306-310 (Jun. 1991).
Preising et al., "A Literature Review: Robots in Medicine", _Engineering in Medicine and Biology (Jun. 1991).
Owen et al., "Endoscopic ligation of perforator leg veins", Lancet, vol. 338, p. 248 (Jul. 27, 1991).
McCollum et al., "A Simple Means of Access for Harvesting the Lesser Saphenous Vein", European Journal Vascular Endovascular Surgery, vol. 5, pp. 469-470 (Aug. 1991).
Feldman, "Laparoscopic Nephrectomy", Journal of Medicine, vol. 325, No. 15, pp. 1110-1111 (Oct. 10, 1991).
Nowzaradan et al., "Laparoscopic Appendectomy for Acute Appendicitis: Indications and Current Use", Journal of Laparoendoscopic Surgery. vol. 1. No. 5, pp. 247-257 (Oct. 1991).
Spaw et al., "Laparoscopic Hernia Repair: The Anatomic Basis", Journal of Laparoendoscopic Surgery, vol. 1, No. 5, pp. 269-277 (Oct. 1991).
Stierli et al., "In Situ Femorodistal Bypass: Novel Technique for Angioscope-Assisted Intraluminal Side-Branch Occlusion and Valvulotomy. A preliminary Report", British Journal of Surgery, vol. 78, No. 11, pp. 1376-1378 (Nov. 1991).
Bailey et al., "Combined Laparoscopic Cholecystectomy and Selective Vagotomy", Surgical Laparoscopy & Endoscopy, vol. 1, No. 1, pp. 45-49 (1991).
Bergamini et al., "Experience with in situ saphenous vein bypass during 1981 to 1989:Determinant factors of long-term patency", p. 137 (1991).
Corbitt, JR., "Laparoscopic Herniorrhaphy", Surgical Laparoscopy & Endoscopy, vol. 1, No. 1, pp. 23-25 (1991).
Cuschieri, "Variable curvature shape-memory spatula for laparoscopic surgery", Surgical Endoscopy, vol. 5, pp. 179-181 (1991).
Fitzgibbons et al., "Open Laparoscopy", Surgical Laparoscopy, pp. 87-97 (1991).
Fowler et al.., "Laparoscopy-Assisted Sigmoid Resection", Surgical Laparoscopy & Endoscopy, vol. 1, No. 3, pp. 183-188 (1991).
Gazayerli, "The Gazayerli Endoscopic Retractor* Model 1" Surgical Laparoscopy & Endoscopy, vol. 1, No. 2, pp. 98-100 (1991).
Zhila et al., "High Resection of the Left Testicular Vein and Ligation of the Internal Iliac Arteries by Means of Retroperitoneoscope", No. 5 (1991).
Zucker, "Laparoscopic Guided Cholecystectomy With Electrocautery Dissection", Surgical Laparoscopy, pp. 143-182 (1991).
"3rd World Congress of Endoscopic Surgery" (Jun. 18-20, 1992).
Santilli et al., "Comparison of Preoperative Standard Angiography with Preoperative Balloon Occlusion Femoral Angiography of the Lower Extremity", Journal of Investigative Surgery, vol. 6, No. 1, pp. 83-95 (Feb. 1993).
Zucker, Surgical Laparoscopy Update, pp. 59-61 (1993).
Wittens et al., "A New "Closed" In Situ Vein Bypass Technique", European Journal Vascular Endovascular Surgery, vol. 8, pp. 166-170 (1994).
Biglioli et al., "Arterial and Venous Graft Utilization in Reoperative Coronary Artery Surgery", Cardiology and Cardiac Surgery: Current Topics. pp. 399-415 (1993).
Chin et al., "Novel Technique and Instrumentation for Laparoscopic Application of Hemostatic Clips", The Journal of the American Association of Gynecologic Laparoscopists, vol. 1, No. 2, pp. 150-153 (Feb. 1994).
Chin et al., "Gasless Laparoscopy Using a Planar Lifting Technique", Journal of the American College of Surgeons, vol. 178. No. 4, pp. 401-403 (Apr. 1, 1994).
Kavoussi et al., "Telerobotic Assisted Laparoscopic Surgery: Initial Laboratory and Clinical Experience", Urology, vol. 44, No. 1, pp. 15-19 (Jul. 1994).
Van Dijk et al., "A New "Closed" In Situ Vein Bypass Technique Results in a Reduced Wound Complication Rate", European Journal Vascular Endovascular Surgery, vol. 10, pp. 162-167 Aug. 1995).
Lumsden et al., "Subcutaneous, Video-Assisted Saphenous Vein harvest: Report of the first 30 Cases", Cardiovascular Surgery, vol. 4. No. 6, pp. 771-776 (Dec. 1996).

Tighe, Instrumentation for the Operating Room: A Photographic Manual (1994).
Dion et al., "Experimental laparoscopic aortobifemoral bypass", Surgical Endoscopy, vol. 9, pp. 894-897 (1995).
Bowersox et al., "Vascular applications of telepresence surgery: Initial feasibility studies in swine", Journal of Vascular Surgery, vol. 23, No. 2,, pp. 281-287 (Feb. 1996).
Rosenthal, "Endoscopic in Situ Bypass", The Surgical Clinics of North America, vol. 75, No. 4, pp. 703-713 (Aug. 1995).
Nwasokwa et al., "Coronary Artery Bypass Graft Disease", Annals of Internal Medicine, vol. 123, No. 7, pp. 528-545 (Oct. 1995).
Davies et al., "Pathophysiology of Vein Graft Failure: A Review", European Journal Vascular Endovascular Surgery, vol. 9, pp. 7-18 (1995).
Gelijns et al., "From the Scalpel to the Scope: Endoscopic Innovations in Gastroenterology, Gynecology, and Surgery", Sources of Medical Technology: Universities and Industry, vol. V. pp. 67-96 (1995).
Lumsden et al., "Vein Harvest", Endoscopic Plastic Surgery (1995).
Sawaizumi et al., "Endoscopic Microsurgical Anastomosis: Experimental Study of microsurgical anastomosis using an endoscope", Journal of Japan Society of Plastic and Reconstructive Surgery, vol. 15, No. 12, pp. 871-879 (1995).
Tebbetts, Tebbetts Endoplastic Instrument System (1995).
Cusimano, "Minimally Invasive Cardiac Surgery for Removal of the Greater Saphenous Vein", Canadian Journal of Surgery, vol. 39 (Oct. 1996), http://www.cma.ca/index.cfm/ci.
Tevaearai et al., "Minimally Invasive Harvest of the Saphenous Vein for Coronary Artery Bypass Grafting", The Annals of Thoracic Surgery, vol. 63, pp. S119-S121 (1997).
Iafrati et al., "Endoscopic in situ bypass: A gentler dissection", Surgical Endoscopy, vol. 12, pp. 463-465 (1998).
Hannah et al., "Laparoscopic Retropubic Urethropexy", The Journal of the American Association of Gynecologic Laparoscopists, vol. 4, No. 1, pp. 47-52 (Nov. 1996).
EndoCABG System: Innovative instrumentation for endoscopic coronary artery bypass grafting (1996).
Lumsden et al., "Subcutaneous, video-assisted saphenous vein harvest", Perspectives in Vascular Surgery, vol. 7, No. 2, pp. 43-55 (1994).
Allen et al., "Endoscopic Saphenous Vein Harvesting", pp. 265-266 (1997).
McCarthy et al., "Tricuspid Valve Repair with the Cosgrove-Edwards Annuloplasty System", The Annals of Thoracic Surgery, vol. 64, pp. 267-268 (1997).
Jordan et al., "Video-assisted saphenous vein harvest: The evolution of a new technique", Journal of Vascular Surgery, vol. 26, No. 3, pp. 405-414 (Sep. 1997).
Moazami, "Minimally Invasive Greater Saphenous Vein Harvesting for Coronary Artery Bypass Surgery", Surgical Rounds, pp. 94-98 (Mar. 1997).
Johnson et al., "Endoscopic Femoral-Popliteal/Distal Bypas Grafting: A Preliminary Report", Journal of American College of Surgeons, pp. 331-336 (1998).
Pierik et al., "Endoscopic versus open subfacial division of incompetent perforating veins in the treatment of venous leg ulceration: A randomized trial", Journal of Vascular Surgery, vol. 26. No. 6, pp. 1049-1054 (1997).
Davis et al., "Endoscopic Vein Harvest for Coronary Artery Bypass Grafting: Technique and Outcomes", The Journal of Thoracic and Cardiovascular Surgery, vol. 116, No. 2, pp. 228-235(Aug. 1998).
Hallock et al., "An Endoscopic Subcutaneous Dissector for Obtaining Vein Grafts", Annals of Plastic Surgery, vol. 41, No. 6, pp. 595-599 (Dec. 1998).
Morris et al., "Minimally Invasive Saphenous Vein Harvesting", The Annals of Thoracic Surgery, vol. 66, pp. 1026-1028 (1998).
Allen et al., "Endoscopic Versus Traditional Saphenous Vein Harvesting:A Prospective, Randomized Trial", pp. 26-31 (1998).
Stavridis et al., "Minimally Invasive Long Saphenous Vein Harvesting Using a Laryngoscope", The Heart Surgery Forum. vol. 1, pp. 37-40 (Jan. 30, 1998).
Tran et al., "Tunneling versus open harvest technique in obtaining venous conduits for coronary bypass surgery", European Journal of Cardo-thoracic Surgery, vol. 14, pp. 602-606 (1998).
Wilson, "Ethicon Endopath System", Minimally Invasive Vein Harvesting the Second Generation (Jun. 1998).
"Resins Aid in Bypass Surgery", Plastics Engineering, vol. LIV, No. 8 (Aug. 1998).
Dregelid et al., "Endothelial cell injury in human saphenous veins after manipulation and tweezer grasping", Journal of Cardiovascular Surgery, vol. 29, pp. 464-469 (1988).
Voellinger et al., "Video-Assisted Vein Harvest: A Single Institution's Experience of 103 Peripheral Bypass Cases", Vascular Surgery, vol. 32. No. 6, pp. 545-557 (Nov./Dec. 1998).
Akbari et al., "Saphenous Vein Bypass to Pedal Arteries in Diabetic Patients", pp. 227-232 (1998).
Belkin et al., "Nonreversed Saphenous Vein Bypass for Infrainguinal Arterial Reconstruction", Techniques in Vascular Endovascular Surgery, pp. 233-241 (1998).
Kulbaski et al., "Video-Assisted Saphenous Vein Harvest", Techniques in Vascular and Endovascular Surgery, pp. 91-102 (1998).
Kyo et al., "Endoscopic harvest of saphenous vein graft for coronary artery bypass grafting: Saitama—Olympus technique", European Journal of Cardio-thoracic Surgery, vol. 14. Suppl. 1, pp. S94-S99 (1998).
Lacroix et al., "Classic versus Endoscopic Perforating Vein Surgery:a Retrospective Study", Acia chir bieg, vol. 98, pp. 71-75 (1998).
Stoney et al., "Lower Extremity", Comprehensive Vascular Exposures, pp. 145-182 (1998).
Brown et al., "Heparin Reduced Residual Clot Within the Lumen of Endoscopically Harvested Saphenous Veins", http://www.aats.org/annualmeeting/Abstracts/2007/T7.html (Aug. 6, 2008).
Snowden-Pencer, Inc., "Emory Endoplastic Instruments", Endoscopic Plastic Surgery, pp. 1-10 (1993).
Wengrovitz, "Wound Complications of Autogenous Subcutaneous Infrainguinal Arterial Bypass Surgery: Predisposing Factors and Management", vol. 11. No. 1, pp. 156-163 (Jan. 1990).
Iafrati, "Laparoscopic Cholecystectomy in the Community Hospital, our first 101 cases", Current Surgery, vol. 48, No. 10 (Dec. 1991).
Ashby, "Operative Choledochoscopy in Common Bile Duct Surgery", Annals of the Royal College of Surgeons of England, vol. 67, pp. 279-283 (1985).
Nezhat et al., "Salpingectomy via Laparoscopy: a new surgical approach" Journal of Laparoendoscopic Surgery (1991), http://www.ncbi.nlm.nih.gov/pubmed/1834264.
Gershman et al., "Laparoscopic Pelvic Lymphadenectomy", Journal of Laparoendoscopic Surgery, vol. 1, No. 1 (1990).
Leahy et al., "Minimally Invasive Esophagogastrectomy: An Approach to Esophagogastrectomy Through the Left Thorax", Journal of Laparoendosopic Surgery, vol. 1, No. 1, pp. 59-62 (Nov. 1990).
Towbin et al., "Real-Time US Guidance During Renal Biopsy in Children", Journal of Vascular and Interventional Radiology (1991), http://www.ncbi.nlm.nih.gov/pubmed/1797225.
Cooperman et al.., "Laparoscopic Colon Resection: a case report", J. Laparoendoscopic Surgery 1991, http://www.ncbi.nlm.nih.gov/pubmed/1834273.
Gunther, "Percutaneous Interventions in the Thorax", Journal of Vascular and Interventional Radiology, pp. 379-390 (May 1992).
Zuckerman et al., "Splenopneumopexy: evaluation with splenoportography", Journal of Vascular and Interventional Radiology. vol. 3. No. 1 (Feb. 1992), http://www.ncbi.nlm.nih.gov/pubmed/1540718.
Tyler, "Voluntary Sterilization", American Journal of Public Health, vol. 63, No. 7, pp. 573-575 (Jul. 1973).
Yeager et al., "Surgical Management of Severe Acute Lower Extremity Ischemia", Journal of Vascular Surgery, vol. 15, No. 2, pp. 385-393 (Feb. 1992).
Woelfle et al., "Technique and Results of Vascular Endoscopy in Arterial and Venous Reconstructions", Annals of Vascular Surgery, vol. 6, No. 4, pp. 347-356 (Jul. 1992).
Stierli et al., "Angioscopy-guided semiclosed technique for in situ bypass with a novel flushing valvulotome: Early results", Journal of Vascular Surgery. vol. 15. No. 3, pp. 564-568 (Mar. 1992).

Stahlfeld et al., "Letter to the editor: A simple technique to protect subcutaneous grafts", Journal of Vascular Surgery, p. 1080 (Jun. 1992).

Shah et al., "Is long vein bypass from groin to ankle a durable procedure? An analysis of a ten-year experience", Journal of Vascular Surgery, vol. 15 (1992).

Rosenthal et al., "Endovascular infrainguinal in situ saphenous vein bypass: A multicenter preliminary report", Journal of Vascular Surgery, vol. 16 (1992).

Pietrafitta et al., "An Experimental Technique of Laparoscopic Bowel Resection and Reanastomosis", Surgical Laparoscopy & Endoscopy. vol. 2. No. 3, pp. 205-211 (Sep. 1992).

Pier et al., "Laparoscopic Appendectomy in 625 Cases: From Innovation to Routine", Surgical Laparoscopy & Endoscopy. vol. 1. No. 1 pp. 8-13 (1991).

Pearce et al., "The Use of Angioscopy in the Saphenous Vein Bypass Graft", Technologies in Vascular Surgery, pp. 289-294 (1992).

Narayanan et al., "Experimental Endoscopic Subcutaneous Surgery", Journal of Laparoendoscopic Surgery, vol. 2, No. 3. pp. 179-183 (1992).

McPherson et al., "Intravascular Ultrasound: Principles and Techniques", Technologies in Vascular Surgery, pp. 233-241 (1992).

Jugenheimer et al., "Endoscopic Subfascial Sectioning of Incompetent Perforating Veins in Treatment of Primary Varicosis". World Journal of Surgery, vol. 16, pp. 971-975 (1992).

Harward et al., "The use of arm vein conduits during infrageniculate arterial bypass", Vascular Surgery (1992).

Flinn et al., "A comparative study of angioscopy and completion arteriography after infrainguinal bypass", Tehcnologies iin Vascular Surgery, pp. 295-305 (1992).

Dries et al., "The Influence of Harvesting Technique on Endothelial Preservation in Saphenous Veins", Journal of Surgical Research, vol. 52, No. 3, pp. 219-225 (Mar. 1992).

Taylor et al., "Technique of Reversed Vein Bypass to Distal Leg Arteries", Techniques in Arterial Surgery, pp. 109-122 (1990).

Taylor et al., "Present status of reversed vein bypass grafting: Five-year results of a modern series", Journal of Vascular Surgery. vol. 11, No. 2, pp. 193-206 (Feb. 1990).

Schmidt et al., "A Canine Model of Intimal Hyperplasia (IH) in Autogenous Vein Grafting: A Preliminary Report", Journal of Investigative Surgery, vol. 3, No. 4, pp. 357-364 (1990).

Sadick, "Treatment of Varicose and Telagiectatic Leg Veins with Hypertonic Saline: A Comparative Study of Heparin and Saline". The Journal of Dermatologic Surgery and Oncology, vol. 16, No. 1, pp. 24-28 (Jan. 1990).

Sadick, "Sclerotherapy of Varicose and Telangiectatic Leg Veins: Minimal Sclerosant Concentration of Hypertonic Saline and Its Relationship to Vessel Diameter", The Journal of Dermatologic Surgery and Oncology, vol. 17, pp. 65-70 (1991).

Lamuraglia et al., "Angioscopy guided semiclosed technique for in situ bypass", Journal of Vascular Surgery, vol. 12, No. 5. pp. 601-604 (Nov. 1990).

Knighton et al., "Saphenous Vein In Situ Bypass", The American Journal of Surgery, vol. 160, pp. 294-299 (Sep. 1990).

Feinberg et al., "The use of composite grafts in femorocrural bypasses performed for limb salvage: A review of 108 consecutive case and comparison with 57 in situ saphenous vein bypasses". Journal of Vascular Surgery (1990).

Beretta et al., "Gastroepiploic artery free graft for coronary bypass", European Journal of Cardiothoracic Surgery, vol. 4. pp. 323-328 (1990).

Troidl, "Surgical Endoscopy and Sonography", Surgical Endoscopy, vol. 4, pp. 41-46 (1990).

Cotton, "Biomedical Engineering in Vascular Surgery", Annals of the Royal College of Surgeons of England, vol. 54, pp. 22-32 (1974).

Crispin, "Arterial Endoscopy", Acta Chirurgica Belgica, No. 1, pp. 59-67 (Jan. 1974).

Plecha, "An Improved Method of Harvesting Long Saphenous Vein Grafts", Archives of Surgery, vol. 108, No. 1 (Jan.-Jun. 1974).

Vollmar et al., "Vascular Endoscopy", The Surgical Clinics of North America, vol. 54, No. 1, pp. 111-122 (Feb. 1974).

Fogarty, "Combined thrombectomy and dilation for the treatment of acute lower extremity arterial thrombosis", Journal of Vascular Surgery, vol. 10. No. 4, 530-534 (Oct. 1989).

Blanco, "Resins Aid in Bypass Surgery", Plastics Engineering (Aug. 1998).

O'Neill, "The Effects on Venous Endothelium of Alterations in Blood Flow Through the Vessels in Vein Walls, and the Possible Relation to Thrombosis". Annals of Surgery. vol. 126. No. 3, pp. 270-288 (Sep. 1947).

Matsumoto et al., "Direct Vision Valvulotomy for Nonreversed Vein Graft", Sugery Gynecology & Obstetrics, vol. 165, No. 2, pp. 180-182 (1987).

Hauer, "Surgery of Perforating Veins", Langenbecks Archive Chirurgie Supplement, pp. 464-465 (1992).

Pierik et al., "Subfascial Endoscopic Ligation in the Treatment of Incompetent Perforating Veins", European Journal Vascular Endovascular Surgery, vol. 9, pp. 38-41 (1995).

Gottlob, "Reconstruction of Venous Valves", Venous Valves: Morphology Function Radiology Surgery, pp. 188-213 (1986).

Berci, "Techiques for improving illumination and recording in endoscopy", Optics and Laser Technology, pp. 31-37 (Feb. 1976).

Berci, Endoscopy today and tomorrow (1976).

Shumacker, "Weglowski's Pioneering Vascular Surgery and Barriers to Progress", Current Critical Problems in Vascular Surgery, vol. 3 (1991).

Buchbinder et al., "B-mode Ultrasonic Imaging in the Preoperative Evaluation of Saphenous Vein", The American Journal, vol. 53. No. 7. pp. 368-372 (Jul. 1987).

Hoffmann, "Die subfasziale, endosopische Laser- Perforantes-Dissektion unter Berucksichtigung auch der lateralen Perforansvenen". Vasomed, vol. 9. No. 5 (1997).

Fischer, "Eine neue Generation der Varizenchirurgie", VASA, Band 20, pp. 311-318 (1991).

Jugenheimer et. al., "Ergebnisse der endoskopischen Perforans-Dissektion", Der Chirurg, pp. 625-628 (Aug. 1991).

Kern et al, "Technique of coronary angioscopy" (2008), http://www.uptodate.com/patients/content/topic.do.

Frazee, "Neuroendoscopy Program" (2008), http://neurosurgery.ucla.edu/body.cfm.

Berci et al., "History of Endoscopy", Surgical Endoscopy, vol. 14, pp. 5-15 (2000).

"Ultrasound and Interventional Techniques", Surgical Endoscopy, vol. 10, No. 1 (Jan. 1996).

"Minimal Invasive Surgery", Surgical Endoscopy: Ultrasound and Interventional Techniques, vol. 10, No. 1 (Jan. 1996).

"The Eyes of the Wolf are Sharper", Surgical Endoscopy: Ultrasound and Interventional Techniques, vol. 10, No. 3 (Mar. 1996).

"Endoscopic suturing made easy", Surgical Endoscopy: Ultrasound and Interventional Techniques, vol. 9, No. 2 (Feb. 1995).

"Instruments for percutaneous nucleotomy and discoscopy", Surgical Endoscopy: Ultrasound and Interventional Techniques. vol. 3. No. 1 (1995).

"Fiberscope for vascular endoscopy", Surgical Endoscopy: Ultrasound and Interventional Techniques, vol. 3, No. 2 (1989).

"Narrow operative approach, atraumatic examination. The KARL STORZ Neuro-Endoscope", Surgical Endoscopy vol. 3, No. 3 (1989).

"Fiberscope for vascular endoscopy", Surgical Endoscopy vol. 3, No. 4 (1989).

"New: Universal-Neuro-Endoscope. New application possibilities for Neurosurgery", Surgical Endoscopy vol. 4, No. 1 (1990).

Springer book advertisement, Surgical Endoscopy vol. 4, No. 4 (1990).

Richard Wolf advertisement, Surgical Endoscopy, vol. 5, No. 1 (1991).

"Why do open surgery", Surgical Endoscopy, vol. 5, No. 2 (1991).

"Minimally invasive surgery. Operating proctoscope for anal surgery", Surgical Endoscopy, vol. 5, No. 3 (1991).

"Laparoscopic Surgery . . . The Next Generation", Surgical Endoscopy, Vo. 6, No. 2 (1992).

"There's a Revolution in Surgery. USSC was there in the beginning", Surgical Endoscopy, vol. 6, No. 3 (1992).

"Cuschieri Thoracoscopic Instruments", Surgical Endoscopy, vol. 6, No. 4 (1992).
"Laparoscopic has just turned a new corner . . .", Surgical Endoscopy, vol. 6, No. 5 (1992).
"Electronic Video Laparoscopy", Surgical Endoscopy, vol. 6, No. 6 (1992).
"Performing a Nissen just got easier, faster, and cheaper", Surgical Endoscopy, vol. 9, No. 9 (1995).
"Easy entry . . . maximizes safety . . .", Surgical Endoscopy, vol. 9, No. 5 (1995).
"Richard-Allan Medical Has Just Bent the Rules on Endoscopic Cutting", Surgical Endoscopy, vol. 10, No. 9 (1996).
"High quality endoscopic instruments", Surgical Endoscopy, vol. 10, No. 11 (1996).
"Endoscopic Surgery of the Paranasal Sinuses and Anterior Skull Base", Endoscopy, vol. 22, No. 5 (1990).
"Karl Storz—Endoscopes for bronchoscopy", Endoscopy, vol. 23, No. 1 (1991).
"Original Karl-Storz. System Perfection", Endoscopy, vol. 23, No. 3 (1991).
"Minimally invasive surgery Laparascopic cholecystectomy", Endoscopy, vol. 23, No. 4 (1991).
"Greater Visibility, Lighter Weight", Endoscopy, Vo. 23, No. 5 (1991).
"A Different View on Diagnosis: (Toshiba Medical Systems) and 2 Live International Therapeutic Endoscopy Course in Mexico City Oct. 10-12, 1990", Endoscopy, vol. 22. No. 3 (1990).
ProMIS Line: The complete endoscopy program from AESCULAP, Endoscopy, vol. 28, No. 3 (1996).
"Now you can afford to change your point of view", Endoscopy, vol. 27, No. 3 (1995).
"Karl Storz endoscopes for NEODYM-YAG and C02 lasers", E 1990, Endoscopy, vol. 22, No. 1 (1990).
"Endoscopic Ultrasonography: EUS", Endoscopy, vol. 22, No. 2 (1990).
Surgical Laparoscopy & Endoscopy, vol. 1 No. 1 (1991).
Surgical Laparoscopy & Endoscopy, vol. 1, No. 2 (1991).
Surgical Laparoscopy & Endoscopy, vol. 1, No. 3 (1991).
Surgical Laparoscopy & Endoscopy, vol. 1, No. 4 (1991).
Surgical Laparoscopy & Endoscopy, vol. 2, No. 1 (1992).
Surgical Laparoscopy & Endoscopy, vol. 2, No. 2 (1992).
Surgical Laparoscopy & Endoscopy, vol. 2, No. 3 (1992).
Surgical Laparoscopy & Endoscopy, vol. 2, No. 4 (1992).
"Karl Storz Take-apart: the fully cleanable cost-effective, modular instrument solution", Surgical Laparoscopy & Endoscopy, vol. 6. No. 1 (1996).
Cuschieri, "How I Do It", Laparoscopic cholecystectomy (Mar. 1999).
"History of Endoscopy" (2008), http://www.alexea.org/.
"Laparoscopy" (1998), http://www.ehealthmd.com/library/laparoscopy/LAP_whatis.html.
White et al., Coronary Angioscopy, vol. 22, No. 1, pp. 20-25 (1995).
Olympus Endoscopic Accessories Price List, Effective Feb. 15, 1986.
Feldman, "Laparoscopic Nephrectomy", The New England Journal of Medicine, vol. 325, No. 15, pp. 1110-1111 (Oct. 10, 1991).
Kunlin, "Le traitement de l'ischámie arteritique pas la greffe veineuse longue", Revue de Chirurgie, pp. 206-235 (Aug. 1951).
Stanley et al. Autogenous Saphenous Vein as an Arterial Graft:Clinical Status in Stanley JC (ed): Biologic and Synthetic VaScular Prostheses, New York, Gmne and Stratton. Inc. 333-349 (1982).
Cohen et al Indications for Left Ventricular Aneurysmectomy Circulation 1983; 67; 717-722.
Evdokimov et al., "A Combination of Electroacupuncture and Conduction Anesthesia in Operations for Varicose Dilatation of Lower Extremity Veins", ISSN 0042-4625 (1985).
Lofgren Treatment of Long Saphenous Varicosities and Their Recurrence:A Long-Term Follow-Up, Surgery of the Veins, Grune & Stratton (1985).
Meldrum-Hanna et al. An Improved Technique for Long Saphenous Vein Harvesting for Coronary Revascularization, Annals of Thoracic Surgery 1986 42: 90-92.

Gottlob et al. Replacement of Small Veins by Autologous Grafts: Application of an Endothelium-Preserving Technique, *Vasc Endovascular Surg.* 1982: 16: 27 Vienna and New York.
Lukomskii, "Prevention of Post" (1986).
Nagovitsyn, "Endoscopic Coagulation of the Communicating Veins of the Leg in Chronic Venous Insufficiency", Sovetskaia Meditsina, vol. 12, pp. 109-110 (1987).
Buchbinder et al. B-Mode Ultrasonic Imaging in the Preoperative Evaluation of Saphenous Vein, American Surgeon, Jul. 1987, vol. 53. No. 7.
Sottiurari et al. Autogenous Vein Grafts:Experimental Studies, in Stanley JC (ed): Biologic and Synthetic Vascular Prostheses, New York, Gmne and Stratton, Inc. 311-331 (1982).
Hauer, "Operationstechnik der Endoskopischen Subjascialen Discision der Perforansvenen", Chirurg, vol. 58, pp. 172-175 (1987).
Nagovitsyn, "Endoscopic Electrocoagulation of the Communicating Crural Veins", Khirurgiia (Mosk), vol. 12, pp. 60-61 (Dec. 1987).
Devambez et al., "Ecarteur Autostatique Pour Chirurgie de Varices", Phlebologie: Bulletin de la Societe Francaise de Phlebologie (1988).
Nagovitsyn, "Vein-sparing operations combined with endoscopic electrocoagulation of the communicating veins", Vestnik Khirurgii. vol. 140. No. 3, pp. 92-93 (Mar. 1988).
Nagovitsyn, "Prevention of complications for endoscopic correction of the crural venous blood flow", Vestnik Khirurgii, vol. 142. No. 3, pp. 113-115 (Mar. 1989).
Bailey et al., "Laparoscopic Cholecystectomy: Experience with 375 Consecutive Patients", Ann. Surg. (Oct. 1991).
Maignien, "Splénectomie par voie coelioscopique 1 observation", La Presse Médicale (Dec. 21-28, 1991).
Moll, "Historische Anmerkungen zur Entwicklung von Endoskopie and minimal invasiver Operations-technik", Geschichte der Medizin (1993).
Markstrom, "Intraoperativ angioskopi via infrainguinal bypass med vena saphena magna in situ", Medicinsk Rapport, vol. 89. No, 49 (1992).
Fischer, "Die chirurgishe Behandlung der Varizen Grundlagen and heutiger Stand: Surgery of Varicose Veins", Scheweiz. Rundshau Med. (PRAXIS), vol. 79. No. 7 (1990).
Devambez et al., "Self-Retaining retractor for surgery of varices", Phlebologie, vol. 41, No. 2, pp. 297-299 (1988).
*Endoscopy* [vol. 22, No. 4, 1990]: Document in German language 1990.
Vandamme, Jean-Pierre and Bonte, Jan, Vascular Anatomy in Abdominal Surgery, Thieme Medical Publishers, Inc. New York (1990).
Swobodnik, Atlas of Ultrasound Anatomy, Thieme Medical Publishers, Inc., New York (1991).
Respondent Terumo Cardiovascular Systems Corporation's Supplemental Responses to Maquet Cardiovascular L.L.C.'s Interrogatory Nos. 29. 32-33. 45-46. 51-62, 64 and 78 [redacted version with attached claim charts] Aug. 15, 2008.
Terumo's Proposed Claim Construction Oct. 31, 2008.
Maquet's Proposed Claim Constructions Oct. 31, 2008.
Maquet's Proposed Claim Constructions with Supporting Authority Nov. 19, 2008.
Public Complaint of Maquet Cardiovascular L.L.C. Under Section 337 of the Tariff Act of 1930 as Amended w/all exhibits Apr. 1, 2008.
Public Response of Respondents Terumo Corporation and Terumo Cardiovascular Systems Corporation to the Complaint and Notice of Investigation Jun. 9, 2008.
Public Amended Response of Respondents Terumo Corporation and Terumo Cardiovascular Systems Corporation to the Complaint and Notice of Investigation Oct. 27, 2008.
Respondent Terumo Cardiovascular Systems Corporation's Responses to Maquet Cardiovascular LLC's Seventh Set of Interrogatories (Nos. 91-95) Aug. 15, 2008.
Respondent Terumo Cardiovascular Systems Corporation's I Responses to Maquet Cardiovascular LLC's Third Set of Interrogatories [No. 78] Jun. 30, 2008.
Respondent Terumo Corporation's Responses to Maquet Cardiovascular LLC's Third Set of Interrogatories (No. 78) Jun. 30, 2008.
Respondent Terumo Corporation's Responses to Maquet Cardiovascular LLC's Sixth Set of Interrogatories (Nos. 82-86) Aug. 15, 2008.

Berci, "Endoscopy", 1976, ISBN 0-8385-2216-5.
"Enter a new realm", 2007, by Boston Scientific Corp.
"Vasoview competitive advantage", 2007, by Boston Scientific Corp.
"VasoView HemoPro endoscopic vessel harvesting system", 2007, by Guidant.
Samuels et al., "In Situ Saphenous Vein Arterial Bypass: A Study of the Anatomy Pertinent to its Use in Situ as a Bypass Graft with a Description of a New Venous Valvulatome", The American Surgeon, vol. 34, No. 2, pp. 122-130 (Feb. 1986).
Order Granting/Denying Request for Reexamination from U.S. Appl. No. 90/004,301. Oct. 1, 1996.

File History of U.S. Patent No. Re 36,043 issued on Jan. 12, 1999.
File History of U.S. Appl. No. 10/897,157 filed on Jul. 24, 2004.
File History of U.S. Appl. No. 10/052,016 filed on Jan. 16, 2002.
File History of U.S. Patent No. 7,326,178 issued on Feb. 5, 2008.
File History of U.S. Patent No. 5,993,384 issued on Nov. 19, 1999.
File History of U.S. Patent No. 5,895,353 issued on Apr. 20, 1999.
Decision to merge reexamination and reissue proceedings for U.S. Patent No. 5,373,840 (U.S. Appl. No. 90/004,301). Jan. 17, 1999.

* cited by examiner

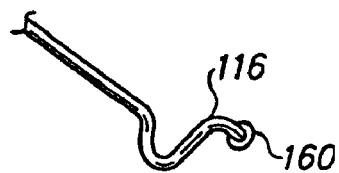
FIG. 9F
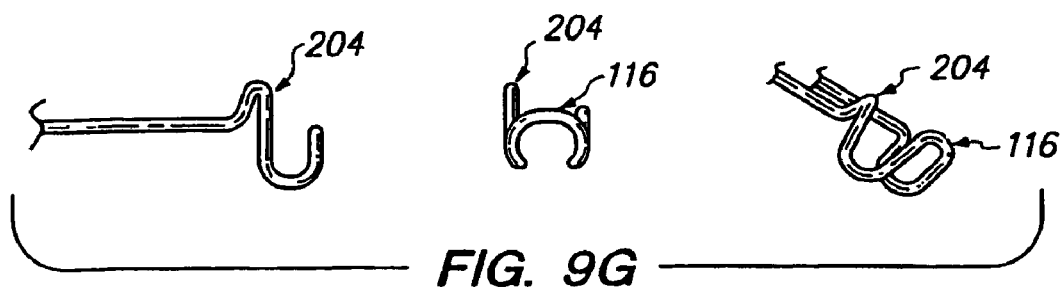
FIG. 9G
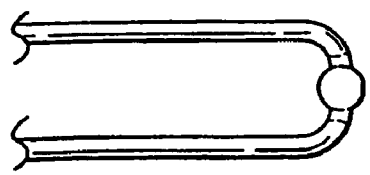 
FIG. 10A            FIG. 10B
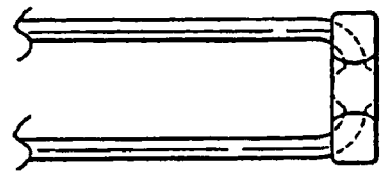 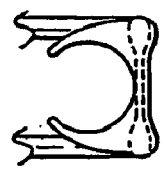
FIG. 10C            FIG. 10D

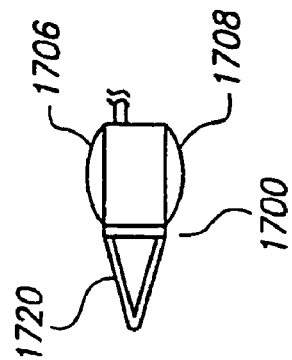
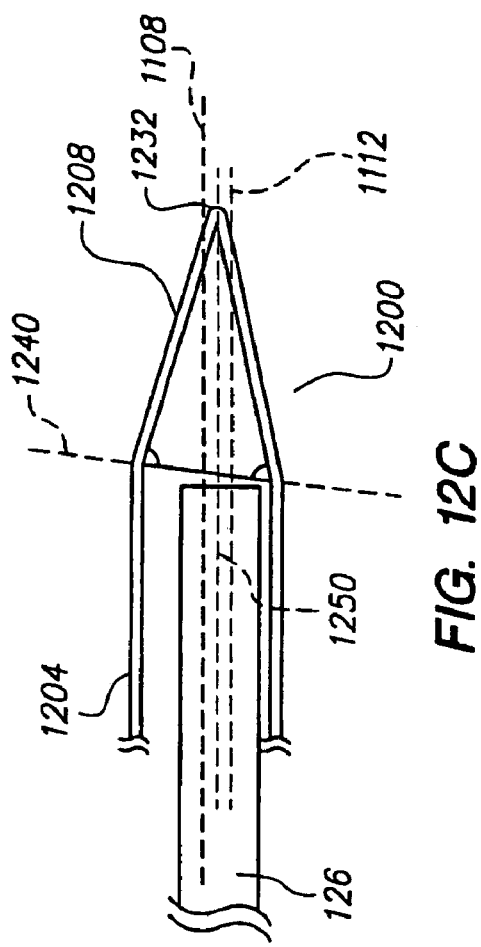
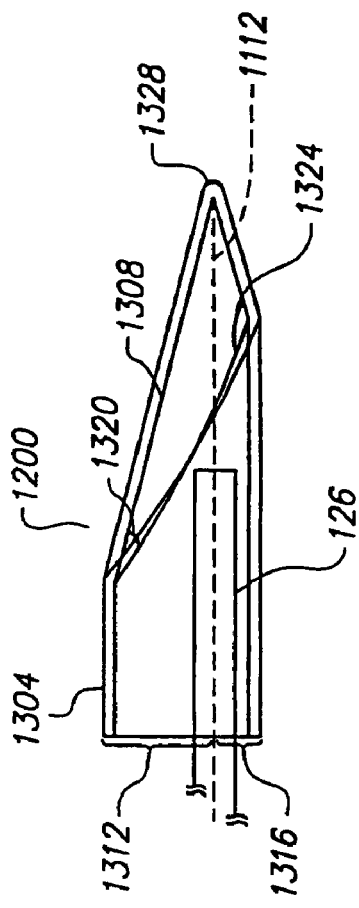

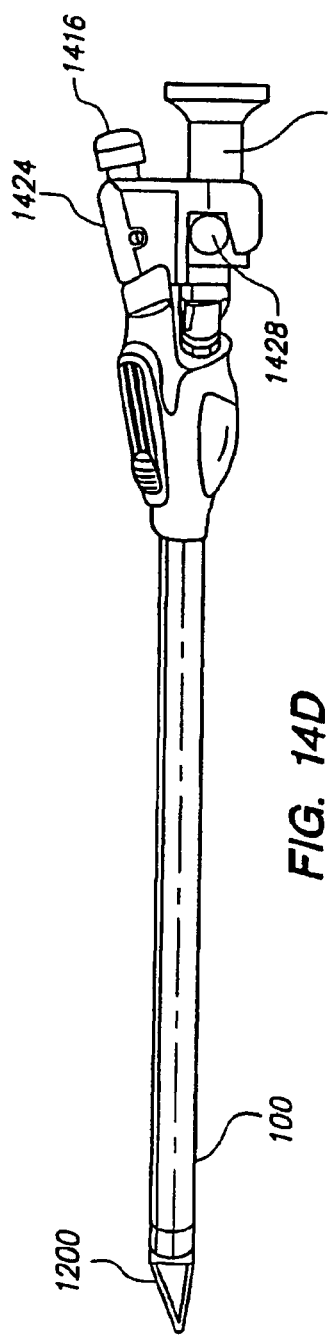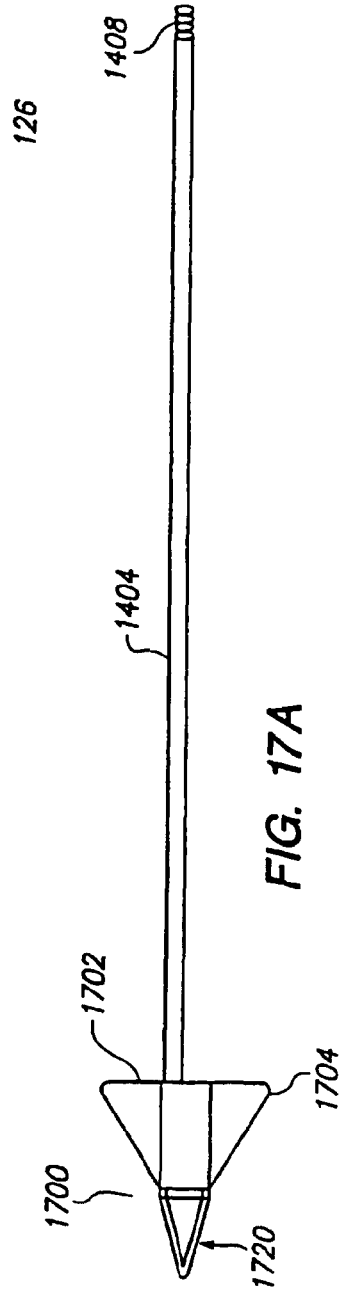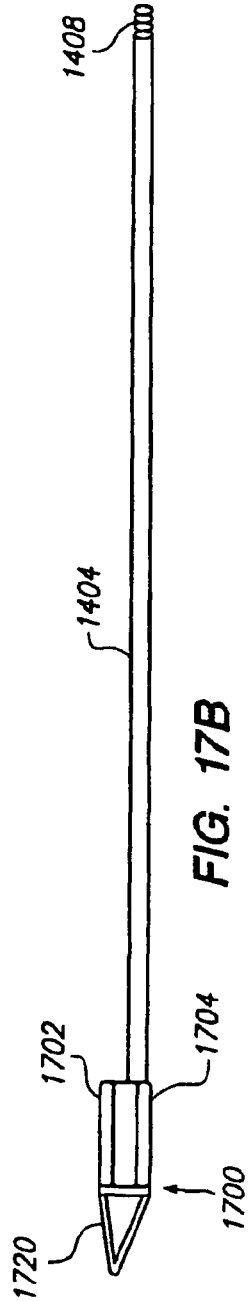
FIG. 14D
FIG. 17A
FIG. 17B

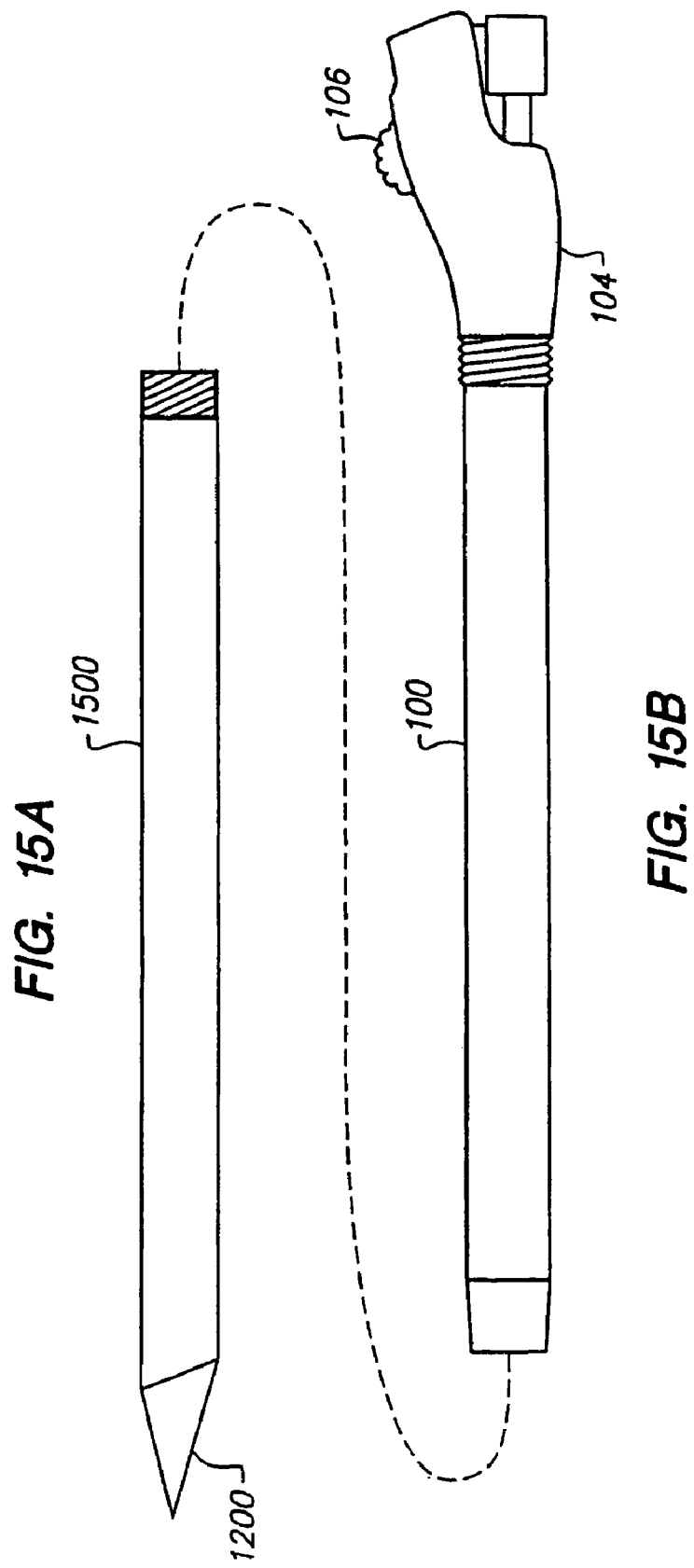

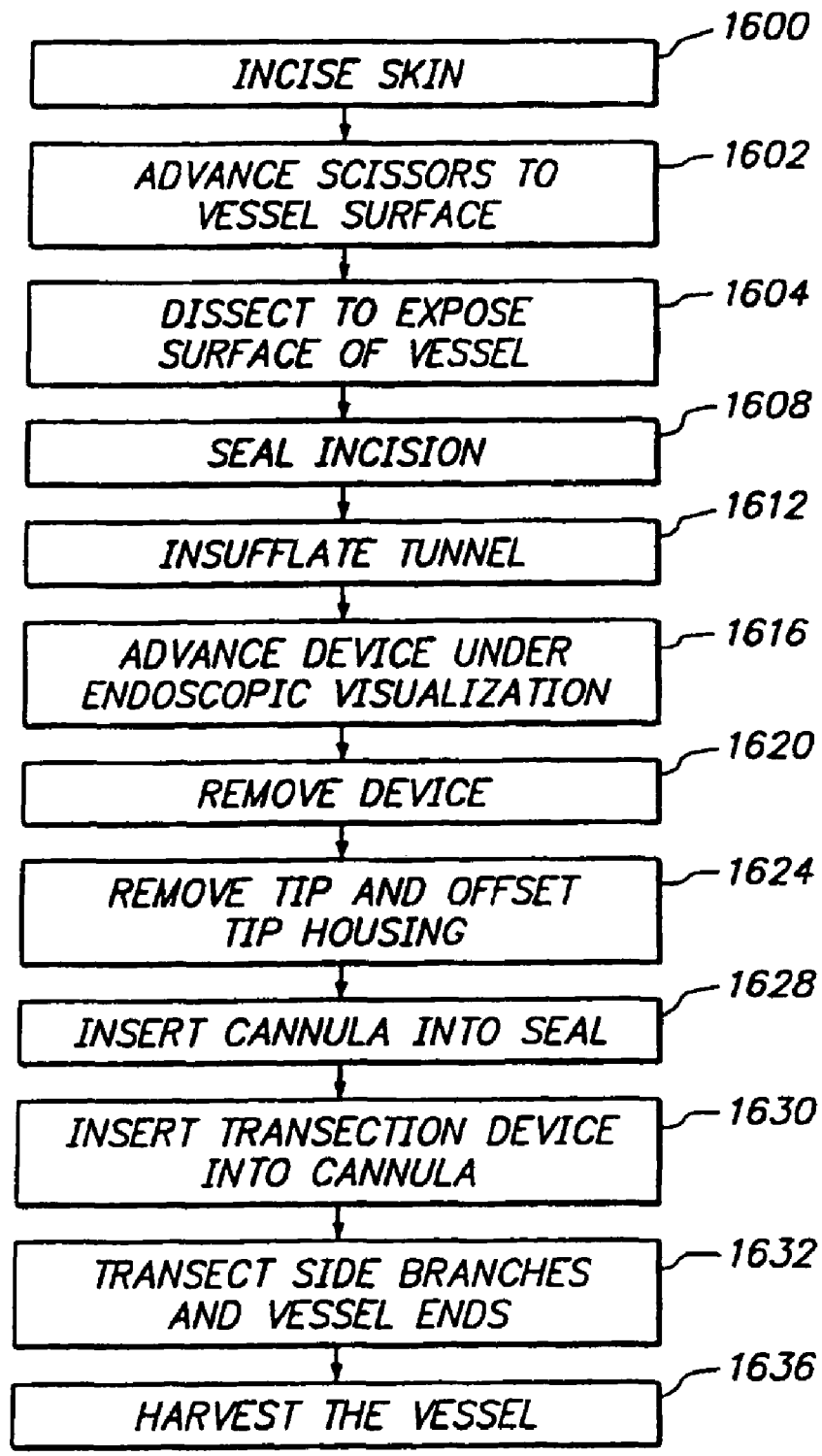

VESSEL RETRACTOR

RELATED APPLICATIONS

The present application is a continuation of application Ser. No. 10/807,368, filed on Mar. 22, 2004, which is a continuation of application Ser. No. 10/218,475, filed on Aug. 12, 2002, now issued as U.S. Pat. No. 6,752,756, which is a continuation of application Ser. No. 09/490,552, filed Jan. 25, 2000, and now issued as U.S. Pat. No. 6,432,044, which is a continuation of Ser. No. 09/227,393, filed Jan. 8, 1999, now abandoned, which is a continuation-in-part application of application Ser. No. 09/102,723 filed on Jun. 22, 1998, now issued as U.S. Pat. No. 5,895,353 and the subject matter hereof is related to the subject matter of application Ser. No. 08/593,533 entitled "Tissue Separation Cannula" filed on Jan. 24, 1996 by Albert K. Chin, now abandoned, which is a continuation-in-part application of application Ser. No. 08/502,494, entitled "Tissue Separation Cannula And Method," filed on Jul. 13, 1995, now abandoned, which prior applications are assigned to the same assignee as the present application and are incorporated herein in their entireties by this reference thereto.

FIELD OF THE INVENTION

This invention relates to a cannula used for vessel retraction, and more particularly to a cannula and method for retracting a vessel during dissection and transection.

BACKGROUND OF THE INVENTION

One important component of a surgical cannula is the tip, disposed on the distal end of the cannula. A properly configured tip can provide important functionality to a cannula. For example, the functions of vessel dissection and transection are commonly performed by two separate instruments. The device described in the pending application Ser. No. 08/907,691, entitled "Tissue Separation Cannula with Dissection Probe and Method," filed on Aug. 8, 1997, discloses a device for separating surrounding connective tissue from a vessel (dissection). The device described in the pending application Ser. No. 09/102,723, entitled Vessel Isolating Retractor Cannula and Method," filed on Jun. 22, 1998, discloses a device for retracting the vessel, ligating side branches, and transecting the branches to allow removal of the vessel. It is desirable to use a single device for performing the above functions.

The construction of a cannula tip also affects the visual field provided to a surgeon through an endoscope. When an endoscope is situated in a lumen of the cannula, the surgeon looks through the endoscope and through the transparent tip to view the surgical site. It is desirable to have a tip which maximizes the visual field of the endoscope.

The cannula tip may also be used to dilate a tunnel or anatomical space through tissue planes. In pending application Ser. No. 09/133,136, entitled "TISSUE DISSECTOR APPARATUS AND METHOD," filed Aug. 12, 1998, assigned to the same assignee as the present application, and which is hereby incorporated by reference, a cannula is constructed with a bulbous element near the tip of the cannula for performing tissue dilation as the cannula is advanced. Cannula tips for dilating tunnels through tissue require force in order to advance the cannula and dilate the tissue. It is desirable to have a tip which can perform tissue dilation or dissection using a minimal amount of force and causing minimal trauma.

SUMMARY OF THE INVENTION

In accordance with the present invention, a tissue retractor is positioned within a cannula with a dissection cradle end of the retractor positioned at the distal end of the cannula. The retractor includes a first portion that has an axis approximately parallel to a central axis of the cannula, and a second portion that has an axis which is at an angle with respect to the central axis of the cannula. The dissection cradle is located at the distal end of the second portion of the retractor. In another embodiment, the retractor includes two legs having substantially parallel axes that selectively protrude from the distal end of the cannula. The protruding legs support the dissection cradle formed in the shape of a loop that is positioned in a plane skewed relative to the axes of the legs, with a bottom of the loop directed away from the cannula. Thus, in operation, when the surgeon locates a vein and side branch of interest, the surgeon extends the retractor to cradle the vein in the dissection cradle. Once cradled, the retractor may be fully extended to urge the vein away from the axis of the cannula, causing the side branch to be isolated and exposed to a surgical tool. The surgical tool may then be extended from within the cannula to operate on the isolated and exposed side branch.

In another embodiment, the top of the loop of the dissection cradle is flat and thin, allowing atraumatic support of the vein, and minimizing contact between the retractor and the surgical tool. In yet a further embodiment, the retractor includes a single leg with the loop formed by the one leg of the retractor, and with a stopper coupled to the distal end of the retractor. In still another embodiment, the cannula comprises a sliding tube which encases the retractor, and in a first position is extended out to encase the second portion of the retractor, and in a second position is extended to encase only the first portion of the retractor. In response to the sliding tube being in the first position, the second and first portions of the retractor are both approximately parallel to the axis of the cannula. In response to the sliding tube being in the second position, the second portion of the retractor is skewed relative to the axis of the cannula.

In accordance with an alternate embodiment of the present invention, a removable, transparent tip is positioned at the distal end of the cannula to provide a single cannula for performing dissection and transection. When attached, the tip seals the distal end of the cannula in a fluid resistant manner. The tip is conical and ends in a sharp interior point and a slightly rounded exterior point which allows the surgeon to bluntly dissect tissue in the area of interest under endoscopic visualization. When tissue dissection is complete, the surgeon can remove the tip from the cannula, and the surgeon is now able to use the cannula to transect side branches and vessel ends. In order to maximize the visual field provided by the endoscope, the tip is configured to allow the apex of the tip to be aligned with the central axis of the endoscope. In one embodiment, a distal end of the tip is tilted in an oblique fashion to allow the apex of the tip to align with or near to the central axis of the endoscope. In an alternate embodiment, the conical end of the tip has unequal taper angles relative to a plane of transition between the cylindrical and conical portions of the tip, thus skewing the position of the apex of the tip into alignment with or near to the central axis of the endoscope.

In another embodiment, wing-like protrusions are provided about the cannula near the tip to dilate tissue surrounding the vessel of interest. In one embodiment, the wing-like protrusions are diametrically aligned in a planar configuration with tapered forward edges extending rearward from near the apex of the tip. The planar configuration of the wing-like dilating protrusions near the tip substantially reduces the resistive force encountered during advancement of the cannula through tissue. The wing-like protrusions are positioned on opposite sides of the tip to dissect tissue to form a cavity that may attain a round cross-section under insufflation, thus providing the same resultant tissue dilation as provided by a solid oval dilator, but with less force required to accomplish the tissue dilation. In an alternate embodiment, the leading edges of the wing-like protrusions are curved in a parabolic configuration away from the distal end of the cannula to provide the necessary dilation.

BRIEF DESCRIPTION OF THE DRAWINGS

FIG. 7b is a side view of the retractor 112 of FIG. 7a.

FIG. 9f illustrates multiple views of a fifth alternate embodiment of cradle 116.

FIG. 9g illustrates multiple views of an embodiment of cradle 116 having a spur.

FIG. 10a illustrates a top view of an embodiment of the cradle 116 of FIG. 9c without a "C" ring.

FIG. 10b illustrates a side view of the cradle 116 of FIG. 10a.

FIG. 10c illustrates a top view of the cradle 116 of FIG. 9c with the "C" ring attached.

FIG. 10d illustrates a side view of the cradle 116 of FIG. 10c.

FIG. 12c illustrates a cut-away side view of an alternate embodiment of offset tip 1200.

FIG. 13 illustrates a cut-away side view of an alternate embodiment of the offset tip 1300.

FIG. 14d illustrates a perspective side view of cannula 100 with offset tip 1200 and offset tip housing 1424.

FIG. 15a illustrates a side view of an alternate embodiment of offset tip 1200.

FIG. 15b illustrates a side view of a cannula 100 modified for use with the offset tip 1200 of FIG. 15a.

FIG. 16 is a flow chart illustrating a method of dissecting and transecting vessels according to the present invention.

FIG. 17a illustrates a top view of an embodiment of an offset tip dilator 1700 according to the present invention.

FIG. 17b illustrates a side view of the embodiment of offset tip dilator 1716 of FIG. 17a.

FIG. 17c illustrates a top view of an alternate embodiment of offset tip dilator 1700.

DETAILED DESCRIPTION OF THE INVENTION

Figure 1:
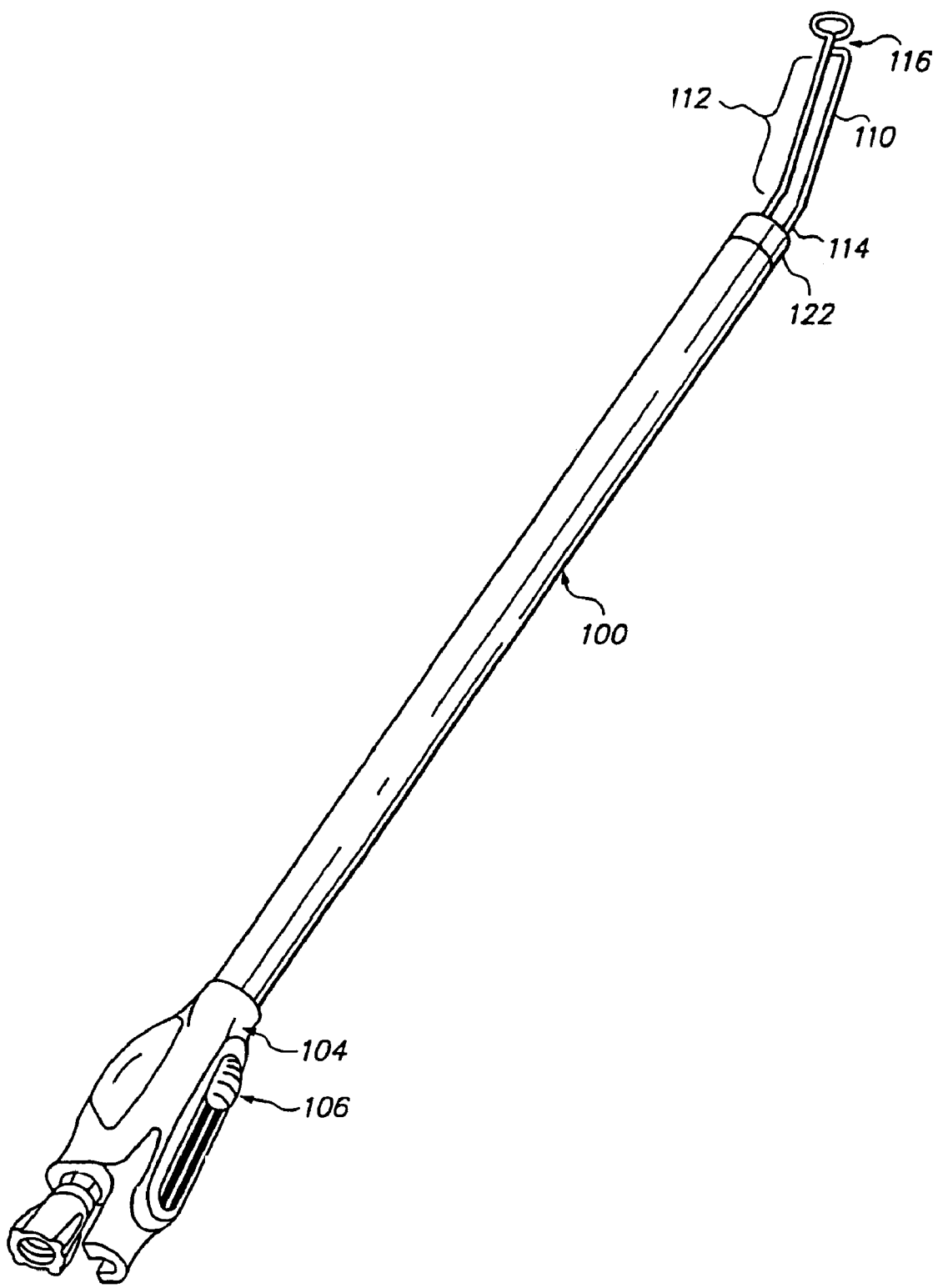
FIG. 1 is a perspective view of a preferred embodiment of cannula 100 showing retractor 112 in an extended position.

FIG. 1 illustrates a perspective view of a preferred embodiment of cannula 100 showing retractor 112 in an extended position. Cannula 100 includes an outer housing 102 of bio-inert material such as polymed UD that may be approximately 12" to 18" in length. The proximal end of the cannula 100 is disposed in handle 104 that includes a button 106 which is coupled to retractor 112 for controlling the translational movement of retractor 112, as described in more detail below.

Figure 2A:
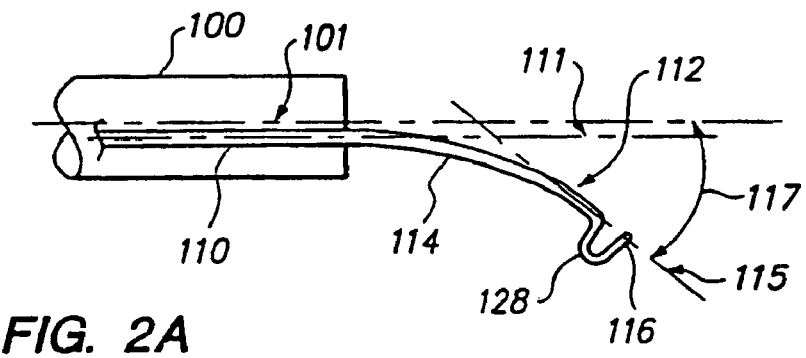
FIG. 2a is a cut-away side view of retractor 112 and cannula 100.

The distal end of the cannula houses a retractor 112, and optionally an endoscope 126 and a surgical tool 120, described below. FIG. 2a illustrates the retractor 112 in more detail. In one embodiment, retractor 112 is formed of resilient wire which has a smooth bend intermediate to a first portion 110 and a second portion 114 of the retractor. The retractor 112 is described as having two portions for ease of description, although the retractor 112 may be formed as an integrated structure. However, retractor 112 may also be manufactured from two separate portions 110, 114 that are coupled together. The first portion 110 of the retractor 112 is positioned within the cannula 100 with the axis 111 of the first portion 110 approximately parallel to the axis 101 of the cannula 100. The second portion 114 is positioned to bend away from the central axis 101 of the cannula. The angle 117 of displacement between the axis 115 of the second portion and the central axis 101 of cannula 100 may be any angle from zero to 180 degrees. The second portion 114 includes a dissection cradle 116 at the distal end of the second portion 114. The retractor 112 may be formed of bioinert material such as stainless steel, or a polymer such as nylon or polyetherimide, or other appropriately strong and resilient plastic. In one embodiment, the retractor 112 includes a coating for lubrication, insulation, and low visual glare using, for example, parylene or nylon 11.

Figure 2B:
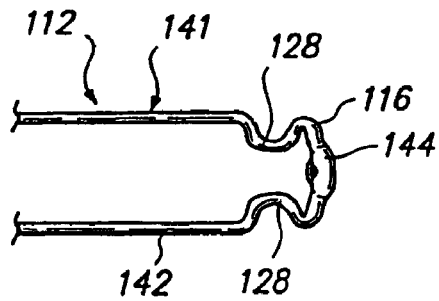
FIG. 2b is a top view of retractor 112.

FIG. 2b illustrates the retractor 112 formed with two legs. The legs 141, 142 of the retractor 112 at the distal end form the dissection cradle 116 in a loop or "U" shape, as shown in FIG. 2a. The top portion 144 of the U-shaped bend is preferably flattened to provide additional surface area for atraumatically supporting a vein 118 or vessel of interest. The side arches 128 of the dissection cradle 116 are used for skeletonizing or dissecting the vein from the surrounding tissues, as well as acting as walls to keep the vessel captured within the arch. The several embodiments of dissection cradle 116 are described in more detail below.

Figure 3A:
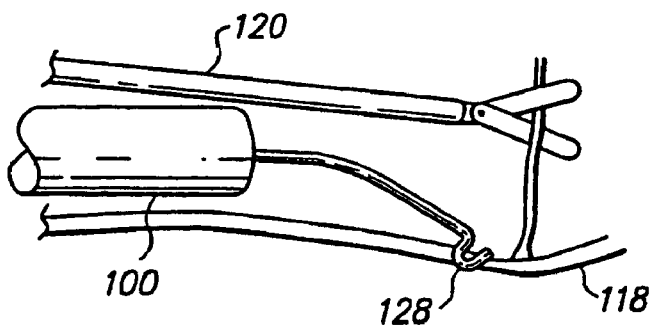
FIG. 3a is a perspective side view of cannula 100 with a sapphenous vein positioned within the cradle 116.

FIG. 3a illustrates a perspective view of the cannula 100 in accordance with the present invention with the retractor fully extended, holding a sapphenous vein 118, and also illustrates an external surgical tool 120 disposed adjacent the cannula 100 for performing a surgical operation, for example, severing a tributary or side branch of the vein 118. The vein is positioned within the side arches 128 of the cradle 116. The dissection cradle 116 may be used to cradle a vein, vessel, tissue or organ of interest, and surgical tool 120 may be any surgical tool suitable for performing a surgical procedure near the dissection cradle 116.

Figure 3B:
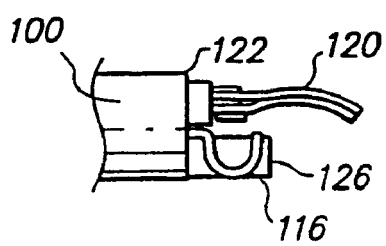
FIG. 3b is a perspective side view of the distal end 122 of cannula 100 in an embodiment in which an endoscope 126 and a surgical tool 120 are present and partially extended.
Figure 3C:
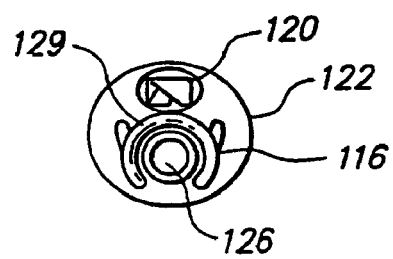
FIG. 3c is a front view of the distal end 122 of cannula 100 in which the surgical tool 120 and the retractor 116 are partially extended, and an endoscope 126 is present.

FIG. 3b illustrates a perspective view of cannula 100 in an embodiment in which the surgical tool 120 is positioned within the cannula 100, and an endoscope 126 is present. In this embodiment, cradle 116 preferably overlays the endoscope 126 with sufficient clearance to facilitate relative movements thereof. However, the endoscope may also be located adjacent the surgical tool 120. In one embodiment, endoscope 126 is positioned with cannula 100 to allow a clear field of view upon extension of the retractor 112. Surgical tool 120 is illustrated as cauterizing scissors, used to sever a tributary or side branch of a sapphenous vein 118. In this embodiment, surgical tool 120 is maximally displaced from the cradle 116 at the cannula end 122. More specifically, as shown in FIG. 3c, the "U"-shaped loop 129 of the cradle 116 is closest to the surgical tool 120. This ensures that a vein 118 or other tissue of interest is retracted away from the surgical tool 120 to facilitate manipulating the surgical tool 120 relative to the side branch or other tissue.

Figure 4A:
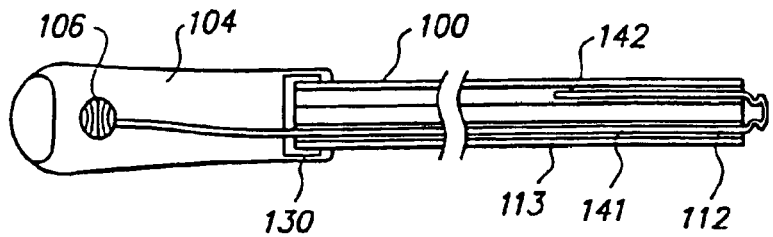
FIG. 4a is a cut-away top view of cannula 100.
Figure 4B:
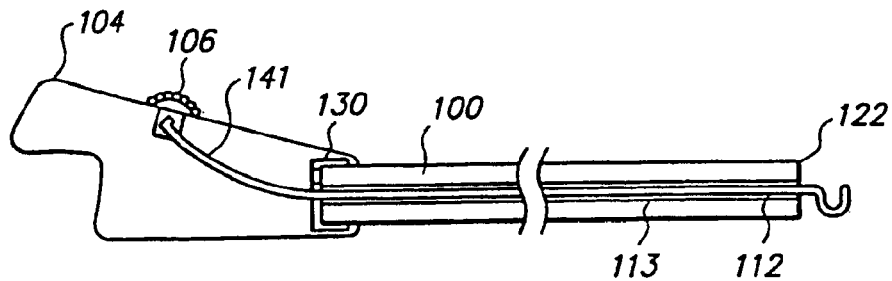
FIG. 4b is a cut-away side view of cannula 100.

FIG. 4a is a cut-away top view of cannula 100. The retractor 112 is slidably positioned within minor lumens 113 along the length of the cannula 100 within close tolerances in order to position the retractor 112 stably within the cannula 100. For example, in one embodiment retractor legs 141, 142 are approximately 0.045 inches in diameter and the lumens 113 encasing the legs 141, 142 are approximately 0.080 inches in diameter, as friction between the legs of the retractor 112 and the lumens 113 holds the retractor stably within the cannula. This configuration restricts rotational movement of the retractor to provide more stable retraction as compared with conventional retractors. The legs 141, 142 of the retractor 112 are formed of flexible, resilient material and are retained within the lumen 113 in substantially straight or flat orientation, but may return to a material bend or curve, as illustrated in FIG. 5a, as the retractor 112 is extended from the distal end of the cannula 100.

The leg 141 of the retractor 112 passes through a sliding gas or fluid seal 130 at the proximal end of the lumen 113. The leg 141 of the retractor 112 passes out of the cannula 100 and into handle 104 for attachment to a slider button 106 for facilitating translational movement of the retractor 112 from the proximal or handle end of the cannula 100. However, other types of control devices such as knobs, grips, finger pads, and the like may be linked in conventional ways to the retractor 112 in order to manually control the translational movement of retractor 112. In one configuration, the proximal end of leg 141 is bent relative to the axis of the cannula, and the button 106 is attached to the bent position of the leg 141 to facilitate moving the button 106 and the retractor 112 translationally under manual control. The button 106 preferably includes lateral grooves to prevent finger or thumb slippage during sliding manipulation of the retractor 112.

Thus, in the operation of a preferred embodiment, a user actuates the slider button 106 to extend retractor 112 out of the lumen 113 at the distal end of the cannula 100. In one embodiment, the resilient retractor 112 is formed in a smooth bend, as shown in FIG. 2a, and gradually deflects away from the central axis 101 of the cannula 100 as the retractor is extended. Upon encountering the target vessel or tissue of interest, the vessel is restrained in the cradle 116, and a lateral resilient force is exerted on the target vessel in a direction away from the cannula. The vessel is thus pushed away from the axis of the cannula 100, isolating it from surrounding tissue or adjacent vessels such as tributaries or side branches. As a tributary is thus isolated, a surgical tool 120 such as cauterizing scissors may be safely employed to operate on the tributary without harming the sapphenous vein 118. When retracted into the cannula 100, the retractor 112 is again resiliently straightened or flattened.

Figure 5A:
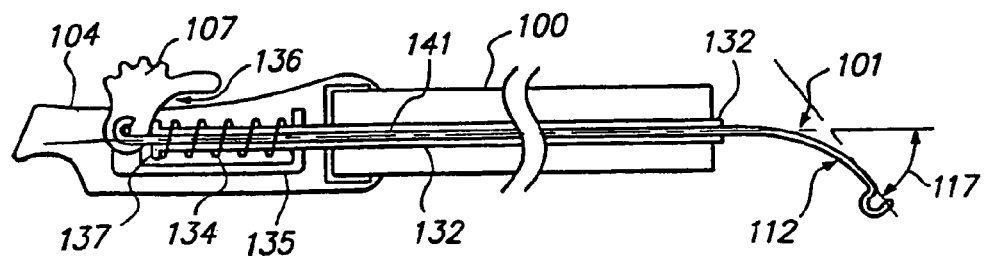
FIG. 5a is a cut-away view of a sliding tube embodiment of cannula 100 in a first position.
Figure 5B:
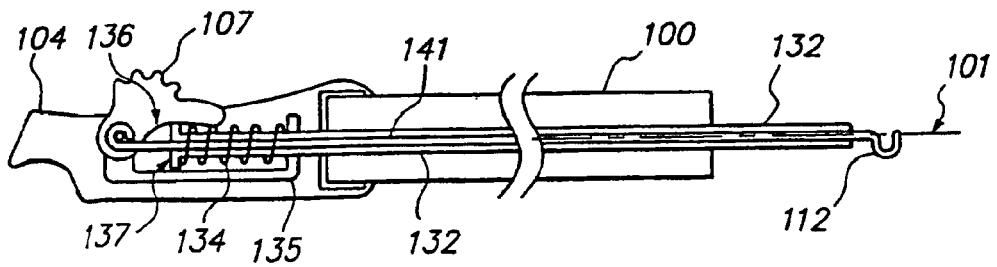
FIG. 5b is a cut-away view of the sliding tube embodiment of FIG. 5a in a second position.

In an alternate embodiment as illustrated in FIGS. 5a and 5b, a sliding tube 132 is added to provide operational versatility to cannula 100. In a first position, the sliding tube 132 is retracted and the retractor 112 protrudes from the distal end at an angle with respect to the central axis 101 of the cannula 100. In a second position, the sliding tube 132 is extended out, temporarily straightening the retractor 112. As illustrated in FIG. 5a, a sliding tube 132, in a first position encases the retractor 112 up to the point at which the retractor 112 curves away from the central axis 101 of the cannula thus allowing the retractor 112 to displace and isolate a target vessel. The proximal end of the sliding tube 132 is linked to button 107 for translationally moving retractor 112 as well as actuating the sliding tube 132. In one embodiment, as illustrated in FIG. 5a, the sliding tube 132 is in a first position with the button 107 in an upright position. A spring 134 is coupled between a support structure 135 and the proximal end 137 of the sliding tube 132. In the first position of sliding tube 132, the spring 134 is extended fully and exerts little or no force on the sliding tube 132. Of course, sliding tube 132 may be manually manipulated without linkage to a button 107.

To extend the sliding tube 100, button 107 is pushed down. As illustrated in FIG. 5b, the button 107 has a cam surface 136 which pushes on the proximal end 137 of the sliding tube 132 as the button 107 is pressed. The sliding tube 132 is pushed forward, overcoming the resilient force of spring 134, to encase the retractor 112 and decrease angle 117 between the distal end of the retractor 112 and the central axis 101 of the cannula 100. Upon releasing the button 107, the spring force urges the proximal end 137 of the sliding tube 132 back toward the first position against button 107. The sliding tube 132 is formed of material having sufficient strength to force the retractor 112 to straighten out the angle 117, and the retractor 112 is formed of resilient material having a sufficient flexibility to straighten out the angle 117 in response to a tube 132 being slid over the retractor 112, but having sufficient rigidity to cradle and dissect a target vessel. Resiliency of the retractor 112 ensures return to the downwardly-curved shape after being released from tube 132. Thus, in accordance with this embodiment, a user may employ the curved retractor for certain applications and employ the straightened form for other applications. A manual actuator may be configured in other ways than button 107 to extend the sliding tube 132 in response, for example, to being pulled up instead of pushed down.

Figure 6A:
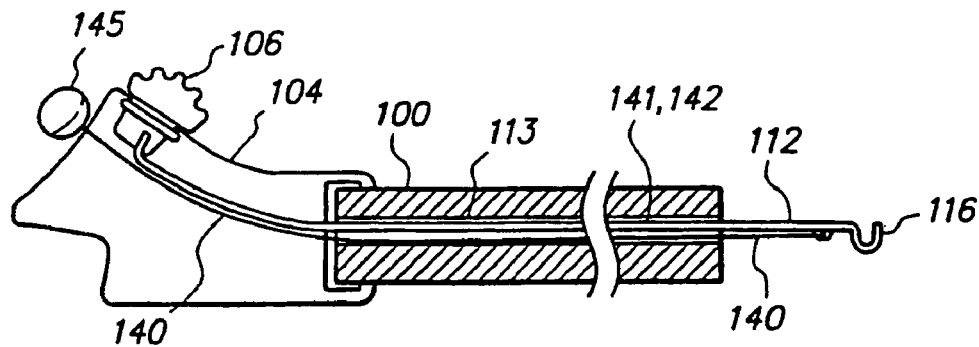
FIG. 6a is a cut-away view of an embodiment of cannula 100 having an angling device 140.
Figure 6B:
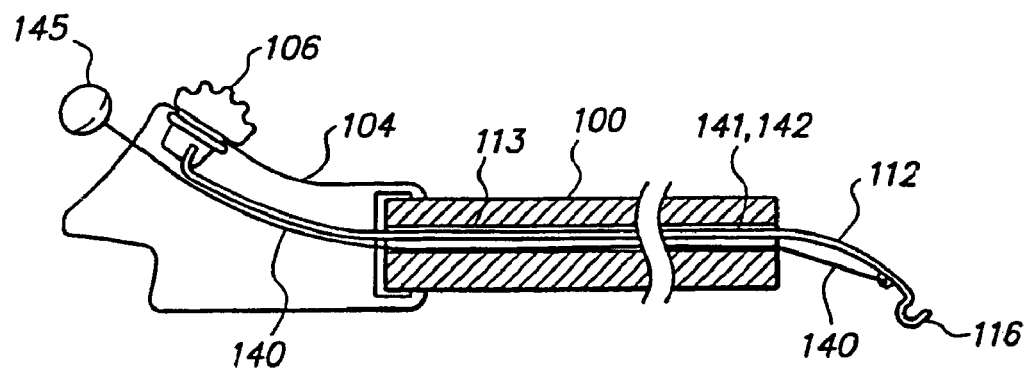
FIG. 6b is a cut-away side view of the apparatus illustrated in FIG. 6a in which the retractor 112 is extended and the angling device 140 is actuated.

Another embodiment employs a retractor 112 which has a naturally straight shape. As illustrated in FIGS. 6a and 6b, an angling device 140 is disposed between the distal end of the retractor 112 and the proximal end of the cannula. The angling device 140 may be positioned within the same lumens 113 as the retractor 112 and preferably may comprise two wires coupled to points below the cradle 116 of the retractor 112 substantially in parallel positions on each of the legs 141, 142.

Figure 6C:
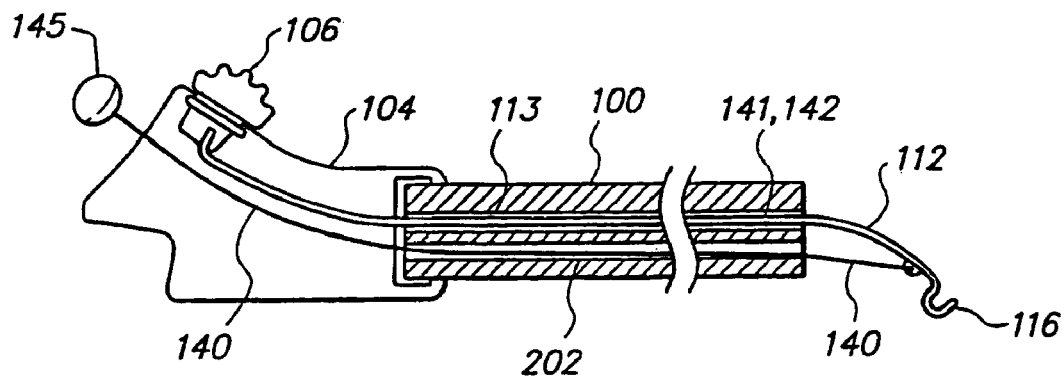
FIG. 6c is a cut-away side view of the angling device embodiment in which the angling device 140 is in a separate lumen from the retractor 112.

Upon extending the retractor 112 using button 106, the angling device 140 is extended with the retractor 112. The angling device 140 is coupled to a handle 145 at the proximal end of the cannula 100 to facilitate establishing an angle in the retractor 112 by pulling with a backward force on the angling device 140. As illustrated in FIG. 6b, after the retractor 112 is extended, the angling device 140 is actuated and a bend is created in the retractor 112 as the backward force exerted on the distal end of the retractor is exerted against the relatively fixed position of the retractor legs 141, 142 disposed within the lumens 113. As shown in FIG. 6c, the angling device 140 may also be located in a separate lumen 202 from the retractor 112 with part of the angling device 140 positioned outside of the cannula 100 when the retractor 112 is in the retracted position.

Figure 7A:
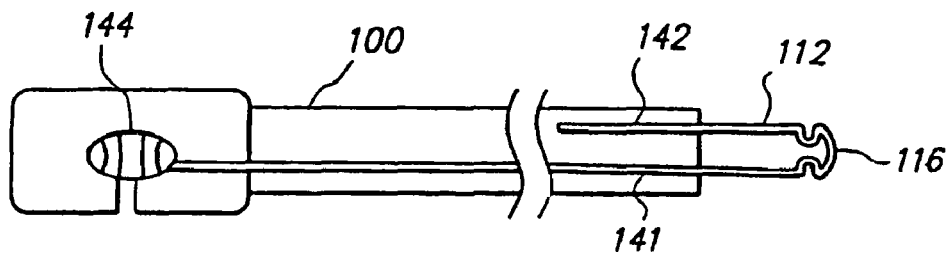
FIG. 7a is a cut-away side view of a twistable retractor 112 in a straight position.
Figure 7C:
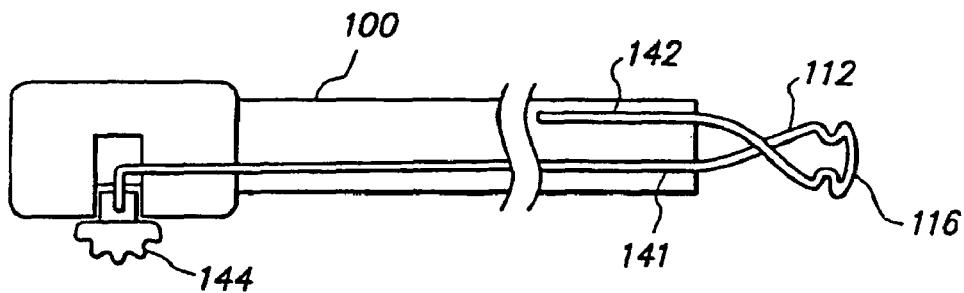
FIG. 7c is a cut-away side view of twistable retractor 112 in a crossed position.
Figure 7B:
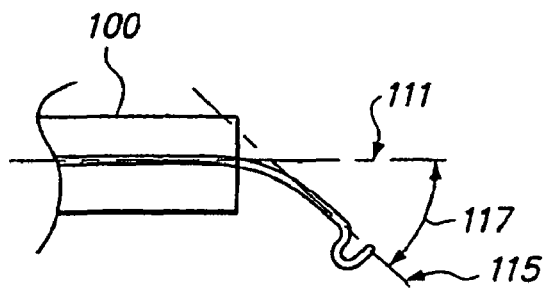
Figure 7D:
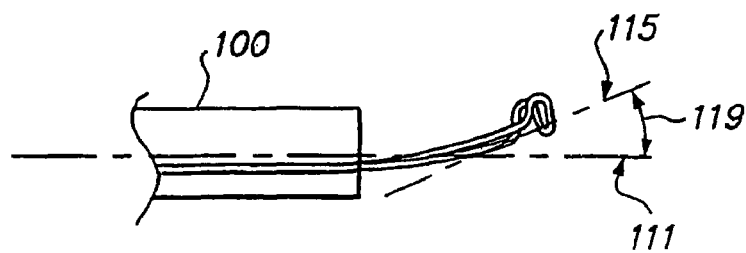
FIG. 7d is a side view of the retractor 112 of FIG. 7c.

FIG. 7a illustrates another embodiment of cannula 100 in which the retractor 112 is pre-formed with one leg 141 of the retractor 112 bent at an angle at its proximal end skewed to the axis of the distal end of the other leg 142. The bent portion of the leg 141 may be linked to a sliding knob 147 for convenient manual manipulation of this embodiment of the invention. Upon sliding the knob 147, the leg 142 coupled to knob 147 is twisted rotationally. The two legs 141, 142 of retractor 112 are coupled together via cradle 116. The axis of the second portion of the retractor 112 in the first position is at a first angle 117 to the axis of the cannula 100, as shown in FIG. 7b. As knob 147 is moved, leg 141 is rotated and crosses under leg 142, as shown in FIG. 7c. This causes cradle 116 to flip 180 degrees and bends the retractor 112 at a second angle 119, as shown in FIG. 7d. Thus, if a vessel is disposed on one side of cradle 116 or cannula 100 while the retractor 112 is in the first position, then upon rotating the knob 147, the vessel is transported to the other side of the cannula 100. This allows the user to isolate the vessel by simply actuating knob 147.

Figure 8A:
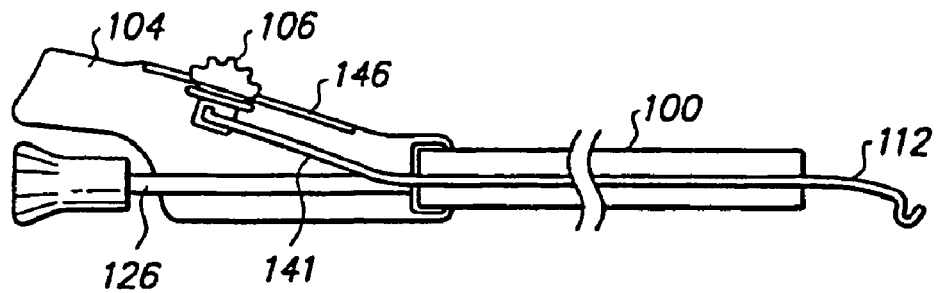
FIG. 8a is a cut-away side view of the handle 104.
Figure 8B:
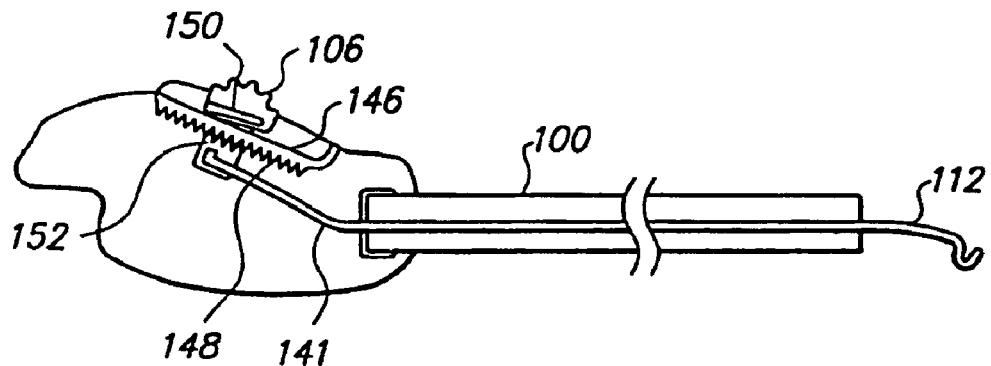
FIG. 8b is a cut-away side view of an alternate embodiment of handle 104.

FIG. 8a illustrates a cut-away side view of button 106 on the handle 104 of cannula 100, with an endoscope 126 positioned within cannula 100. As mentioned above, button 106 is coupled to one leg 141 of the proximal end of retractor 112. Sliding the button 106 in groove 146 translationally moves the retractor 112. Groove 146 is preferably minimally wider than the shaft of button 106 to minimize excessive horizontal movement of button 106 while still allowing smooth translational movement of button 106. As illustrated in FIG. 8b, the button 106 may include locking or ratcheting teeth 152 to give tactile feedback of its location, and to positively retain the button and the associated leg 141 in an extended or retracted position. Several mating teeth 148 are located underneath groove 146, and a spring member 150 is attached to button 106 to exert pressure against the base of groove 146, to engage mating teeth 148, 152. When a force is applied on the top of button 106, the interlocking sets of teeth are disengaged and button 106 can move freely. Upon achieving the desired extension or retraction of the leg 141, button 106 is released and is retained place by the engaged teeth 148, 152.

Figure 9A:
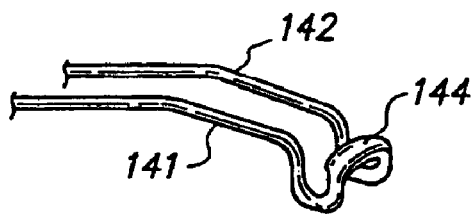
FIG. 9a is a side view of cradle 116.

FIG. 9a illustrates a top view of cradle 116 in an embodiment in which the cradle 116 is formed by two legs 141, 142 of retractor 112. The distal end of the legs form "U"-shaped side guides. The top 144 of the distal portion of the "U" is preferably flattened. This provides atraumatic support for the target vessel retained within cradle 116. Additionally, by minimizing the thickness of distal portion 144, contact with other devices in close proximity with retractor 112 is minimized.

Figure 9B:
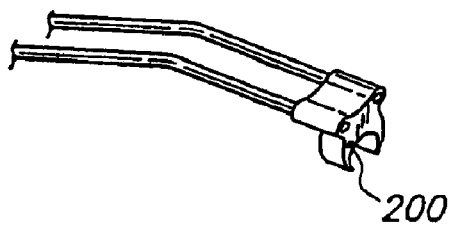
FIG. 9b illustrates a first alternate embodiment of cradle 116.

The cradle 116 may have other effective shapes, for example, as illustrated in FIG. 9b in which a "C" ring element is attached to legs of the cradle 116. The "C" ring may have a small hole 200 in one side with an axis approximately parallel to the axis of the retractor 112. This hole 200 is used to hold suture or other ligating materials, and may also be used as a knot pusher. As shown in FIGS. 10a and 10b, in an alternate embodiment of the embodiment of FIG. 9b, the retractor 112 is formed and flattened and a "C"-shaped ring is coupled to the retractor 112 by, for example, gluing or molding the "C" ring to the distal end of the retractor 112, as shown in FIG. 10c and 10d.

Figure 9C:
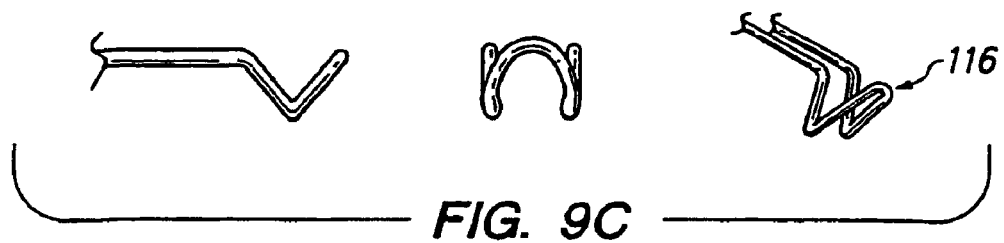
FIG. 9c illustrates multiple views of a second alternate embodiment of cradle 116.
Figure 9D:
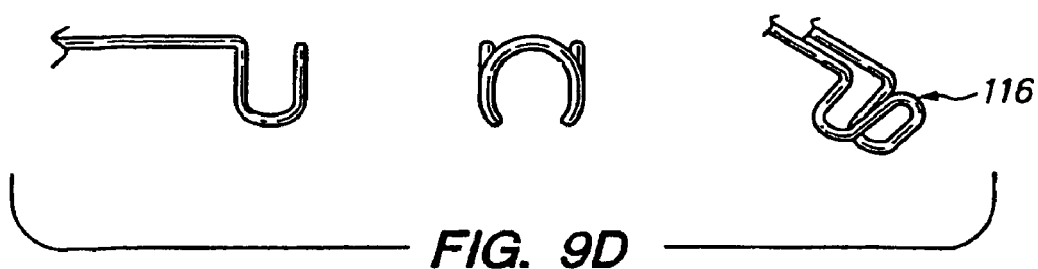
FIG. 9d illustrates multiple views of a third alternate embodiment of cradle 116.
Figure 9E:
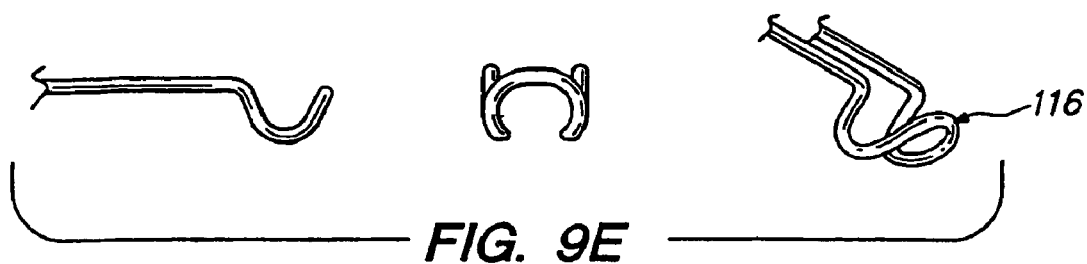
FIG. 9e illustrates multiple views of a fourth alternate embodiment of cradle 116.

Referring back to FIGS. 9c, 9d, and 9e, the side guides of the cradle may include a loop 129 in a "V" shape, an arced "U" shape, or a semi-circular shape. In one embodiment, as illustrated in FIG. 9f, the retractor 112 has only one leg 141, and the cradle 116 is formed by the leg 141. A stopper 160 is coupled to the end of the leg 141 to serve as a guide to retain the target vessel, and add a blunt surface to the end of the wire, for example, for pushing and probing tissue. FIG. 9g illustrates a retractor 112 having a spur 204 formed in one or both legs 141, 142 for allowing the retractor 112 to be used for dissection. Sinusoidal, half-sinusoidal, and other geometric configurations may be used equally effectively as the shape of loop 129 in accordance with the present invention.

Figure 11A:
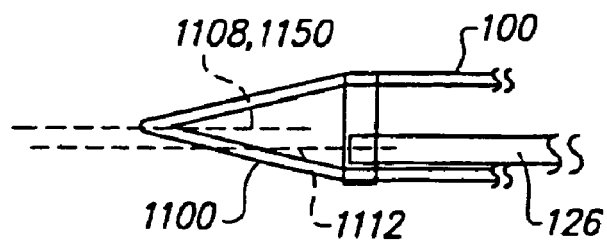
FIG. 11a illustrates a cut-away side view of a tip 1100 in a cannula housing an endoscope 126.

FIG. 11a illustrates a tip 1100 for use with a multi-lumen cannula 100 housing an endoscope 126. The tapered tip 1100 may be removed from, and reattached to the distal end of a cannula 100, as desired. Upon attachment, the tip 1100 seals the distal end of a cannula 100 in a fluid-tight manner. The tip 1100 is configured to provide dissection of the tissue surrounding the vessel of interest, and has a distal radius of approximately 0.045" to reduce the hazard of penetrating the vessel of interest. The inner surface of the tip 1100 tapers to a sharp interior point and a slightly rounded exterior point and the tip 1100 has a uniform wall thickness. The tip 1100 preferably has taper angles of approximately 15° which provides a maximal, undistorted, visual field through an endoscope 126. The tip 1100 tapers outward to a maximal diameter of about 12¾ mm at its shoulder to cover the cannula 100 body which also has a diameter of about 12¾ mm. All of these features allow the tip 1100 to effectively dissect tissue. The tip 1100 of FIG. 11a has a central axis 1150 aligned with the central axis 1108 of the cannula 100. The visual field provided by the endoscope 126, although satisfactory for surgical procedures, is not complete because the endoscope 126 is in a lumen that is offset from the central axis 1108 of the cannula

Figure 11B:
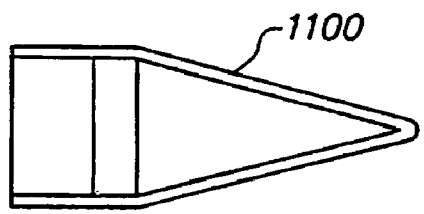
FIG. 11b illustrates a side view of the tip 1100 isolated from cannula 100.

100. The endoscope 126 is offset because of the space required inside the cannula 100 for housing retractors and other instruments in adjacent lumens. FIG. 11*b* illustrates this tip 1100 detached from the cannula 100.

Figure 12A:
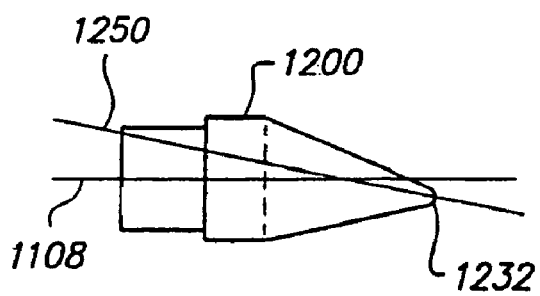
FIG. 12a illustrates a side view of an offset tip 1200 in accordance with the present invention.

FIG. 12*a* illustrates an offset tip 1200 for a cannula 100 in accordance with the present invention. The offset tip 1200 is a transparent, tapered tip as described above for use in endoscopic dissection of a vessel. However, in this embodiment the axis 1250 of the tip 1200 is skewed relative to the central axis 1108 of the cannula 100. The axis 1250 of the tip 1200 is skewed approximately 8°, an angle that is chosen to align the apex 1232 of the tip 1200 with a central axis 1112 of the endoscope 126, as shown in more detail in FIG. 12*b*.

Figure 12B:
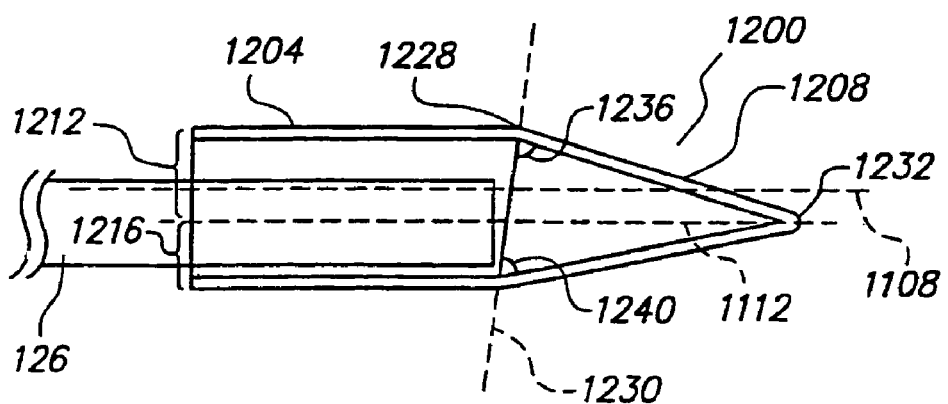
FIG. 12b illustrates a cut-away side view of the offset tip 1200 in a cannula 100 housing an endoscope 126.

FIG. 12*b* illustrates the offset tip 1200 housed in cannula 100 in more detail. The cannula 100 houses a 5 mm endoscope 126 having a central axis 1112 eccentric to the central axis 1108 of the cannula 100. In order to bring the distal end or apex 1232 of the axis of the tapered tip 1200 into the center of the visual field along the central axis 1112 of the endoscope 126, the tapered tip 1200 is tilted or inclined by approximately 8° toward the lumen housing the endoscope 126. This allows the apex 1232 of the tip 1200 to approximately intersect with the central axis 1112 of the endoscope 126. As illustrated in FIG. 12*b*, the tip 1200 is inclined toward the central axis 1112 of the endo scope 126 without altering the taper angles 1236 and 1240 of the side walls. This is accomplished by forming a transition 1228 between the proximal or cylindrical portion 1204 of the tip 1200 and the distal or conical portion of the cannula body 1208 of the tip 1200 substantially along a plane 1230 that is skewed from normal to the central axis 1108 of the cannula 100. The distal portion 1208 of the tip 1200 retains its conical shape and equal taper angles 1228, 1236 between the side walls and the transition plane. The slight extension of the cannula body at the transition plane provides sufficient incline to allow the apex 1232 of the tip 1200 to intersect the central axis 1112 of the endoscope 126. The tip 1200 may be formed of separate conical and cylindrical parts that are attached together, or the tip 1200 may be formed as an integrated structure in the shape thus described.

Alternatively, as shown in FIG. 12*c*, the tip 1200 is inclined at a lesser angle, for example, 5 degrees, toward the axis 1112 of the endoscope 126, positioning the axis 1250 of the distal end 1232 of the tip 1200 intermediate between the central axis 1108 of the cannula 100 and the axis 1112 of the endoscope 126. Positioning the axis 1250 of the tip 1200 to this intermediate point allows the retention of steep conical angles in the tip 1200 which allow for easier advancement of the cannula 100 while using a minimal amount of force. The intermediate positioning also provides a more complete visual field as seen through endoscope 126.

An alternate embodiment of an offset tip 1200 is shown in FIG. 13 in which the taper angles 1320, 1324 of the side walls are selected to form the apex 1328 of the tip 1200 aligned with the central axis 1112 of the endoscope 126. As illustrated, the lower region 1316 of the cylindrical part 1304 extends beyond the upper region 1312 of the cylindrical part at a plane of transition between cylindrical and tapered regions of the tip. However, in this embodiment, the taper angles 1320, 1324 are not equal and the thirty degree angled conical configuration of the tapered part 1308 is not maintained. Rather, the lower taper angle 1324 is increased to an obtuse angle and the upper taper angle 1320 is a reduced acute angle relative to the plane of transition between the cylindrical and tapered portions of the tip. In this configuration of the conical portion 1308, the apex 1328 of the tip 1200 aligns with the central axis 1112 of the endoscope 126. Thus, in accordance with either embodiment, a tip 1200 is provided which allows a maximal visual field to be viewed by the surgeon via the endoscope 126 that is eccentric the central axis 1108 of the cannula 100, but that is aligned with or near to the apex 1232 of the tip 1200.

Figure 14A:
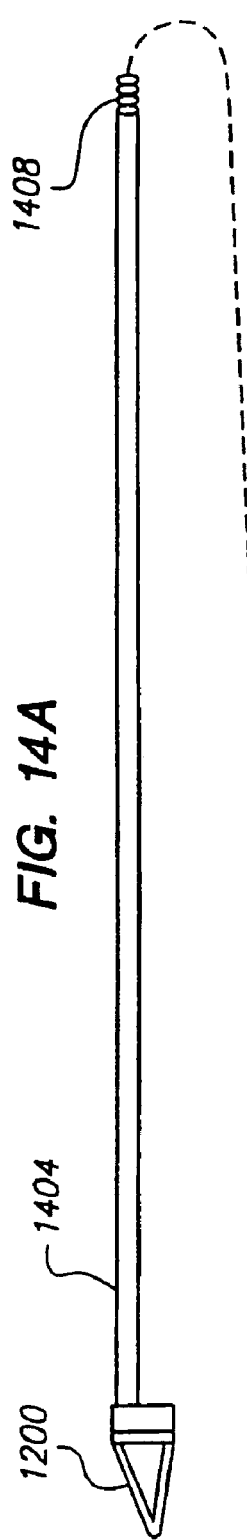
FIG. 14a illustrates a perspective side view of the offset tip 1200 and mounting rod 1404.
Figure 14B:
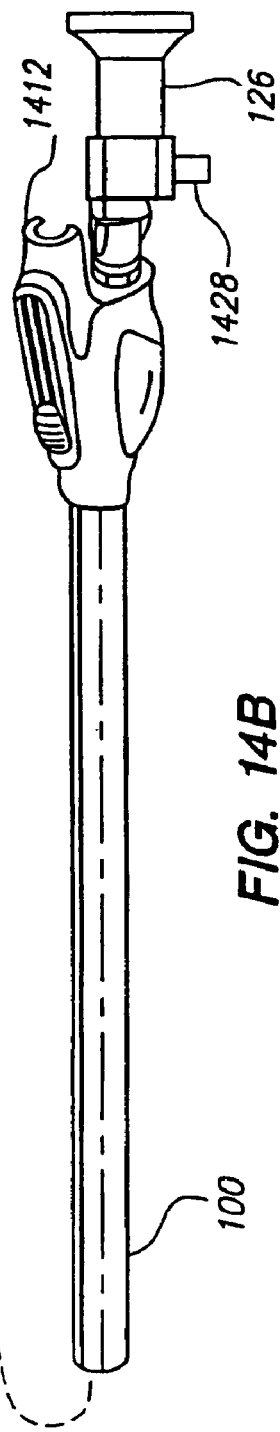
FIG. 14b illustrates a perspective side view of cannula 100 for housing offset tip 1200 and mounting rod 1404.
Figure 14C:
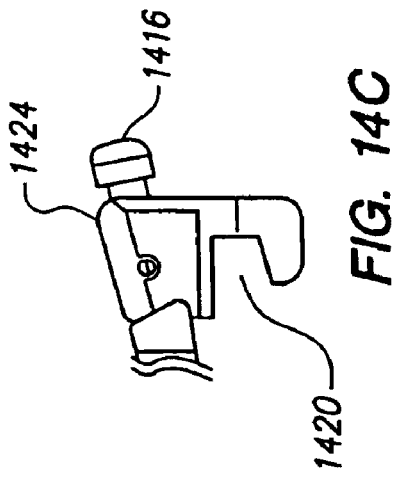
FIG. 14c illustrates a perspective side view of offset tip housing 1424 at the proximal end of the cannula 100.

FIG. 14*a* illustrates a perspective side view of the offset tip 1200 and mounting rod 1404. The tip 1200 is attached to the cannula 100 via the long rod 1404 which extends through an eccentric lumen of the cannula 100, as shown in FIG. 14*b*, and the apex of the tip 1200 is tilted away from the rod 1404 and towards the endoscopic lumen (not shown). The elongated rod 1404 may be attached to the tip 1200, or may be constructed as an integral part of the tip 1200. The elongated rod 1404 preferably is secured in housing 1424, shown in FIG. 14*c*, via threads 1408 on the proximal end of rod 1404 and mating threads within nut or knob 1416. The rod 1404 and housing 1424 abut against the proximal end of the cannula handle 1412, as illustrated in the perspective side view of the assembled device shown in FIG. 14*d*. Referring back to FIGS. 14*a-c*, the housing 1424 includes a slot 1420 configured to slip over the light cable outlet 1428 on the endoscope 126 as assembled within the cannula 100. The housing 1424 preferably contains a rotating nut 1416 which accepts the threaded proximal end 1408 of the rod 1404. When tightened onto the rod 1404, as shown in FIG. 14*d*, the housing 1424 prevents the cannula 100 from rotating about the endoscope 126 by holding the endoscope 126 fixed with respect to the handle 1412. This allows the operator to maintain the correct orientation of the endoscope 126 on the vessel. If the endoscope 126 is allowed to rotate freely, the image may turn sideways or upside down without the operator realizing it, and injury may occur to the vessel if the cannula 100 is advanced in the wrong direction.

Figure 14F:
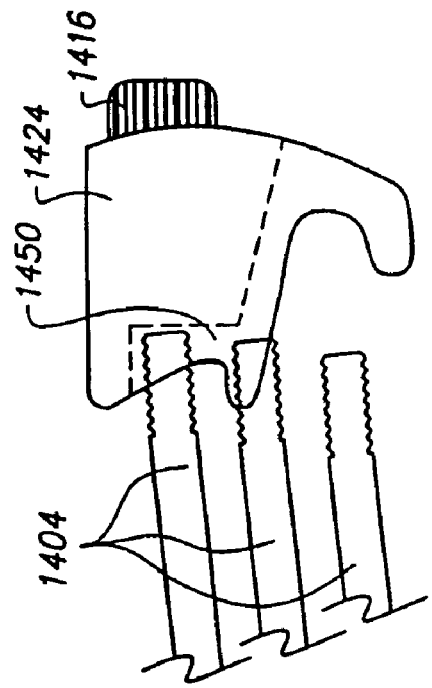
FIG. 14f illustrates a cut-away side view of the offset tip mounting 1424 of FIG. 14e.
Figure 14E:
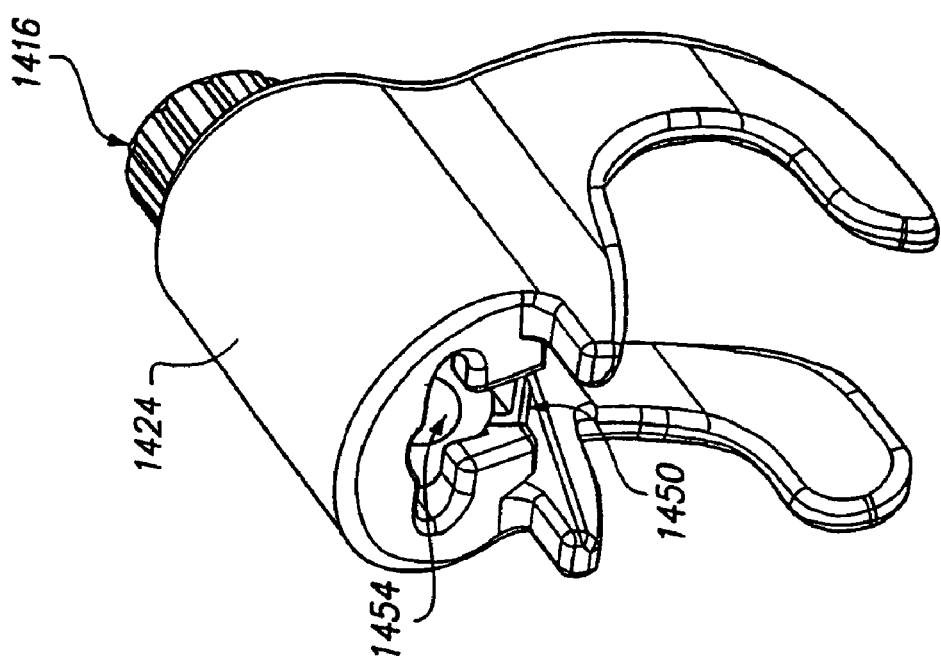
FIG. 14e illustrates a perspective side view of an alternate embodiment of offset tip mount 1424.

In one embodiment, as shown in FIGS. 14*e* and 14*f*, the elongated rod 1404 slips into the housing 1424 via a groove 1450 near its proximal end, and passes through the main hole 1454 in the housing 1424. The groove 1450 allows for the housing 1424 to cover the proximal end of the mounting rod 1404 without completely clearing the most proximal tip of the mounting rod 1404. This allows more room for attaching the housing 1424 which lies between the elongated rod 1404 and additional optical components. The rod 1404 may contain an elastic section, or the rod 1404 may be somewhat elastic along its entire length to facilitate stretching the rod 1404 and pulling it into position in the slot 1454 on the housing 1424, while locking the tip 1200 in place. The elastic force also facilitates sealing the tip 1200 against the distal face of the cannula body.

FIGS. 15*a* and 15*b* illustrates an alternate embodiment of offset tip 1200 and cannula 100. In this embodiment, offset tip 1200 is formed with an elongated case 1500 which slides over the cannula body 100 and locks to the proximal end of cannula 100. In this embodiment, proximal end of cannula 100 is threaded and allows a threaded proximal section of elongated case 1500 to mate securely to the cannula 100.

In a surgical procedure using the tissue-dissecting cannula of the present invention, the surgeon first incises 1600 the skin overlying a vessel of interest to expose the vessel as an initial step of the procedure illustrated in the flow chart of FIG. 16. A scissor tool is inserted 1602 into the incision to create a path to the vessel by dissecting the overlying tissue. Next, the tip 1200 of the cannula 100 is inserted 1604 into the incision to bluntly dissect tissue to form an initial tunnel along the vessel from the incision. The incision is then sealed 1608 using a blunt tip trocar and a tunnel is insufflated 1612. The cannula is advanced 1616 along the vessel to dissect tissue adjacent the vessel under endoscopic visualization through the transparent tip. The offset tip 1200 with the apex thereof in alignment with the endoscope 126 provides a full visual field for the surgeon as the cannula 100 is advanced. The conical end of the tip 1200 dissects the tissue as the cannula 100 is advanced along the vessel. The surgeon dissects both on the anterior and posterior sides of the vessel to create a full 360 degree tunnel around the vessel. Once a selected surgical site is reached, the cannula 100 is removed 1620 from the incision seal and the tip 1200 is removed 1624 from the cannula 100. In one embodiment, as described above, the tip 1200 is removed by unscrewing the threaded portion 1408 of the rod 1404 from the rotating nut 1416. The tip housing 1424 itself is also removed in this embodiment. Insufflation is maintained and the cannula 100 without tip 1200 is inserted 1628 into the seal into the tunnel adjacent the vessel. Transecting devices are then inserted 1630 into the cannula 100. Without tip 1200 disposed over the distal end, the cannula 100 can now be used for transecting 1632 side branches and the ends of the vessel of interest using endoscopic instruments that are selectively installed and removed within instrument lumens in the cannula body 100. After these procedures are completed, the vessel may be removed 1636.

FIG. 17a illustrates another embodiment of an offset tip dilator 1700. In this embodiment of the present invention, the tip 1700 also includes wing-like protrusions for enlarging or dilating a peri-vascular cavity in the course of separating a vessel from adjacent connective tissue. For example, after tissue dissection with an offset tip 1200 to form a tunnel or working cavity adjacent a target vessel by dissecting along the anterior and posterior sides of the vessel, the cannula 100 is removed from the distal end of the body, the offset tip 1200 is detached, and a second tip 1700 is attached to the distal end of the cannula body 100. In one embodiment, the second tip 1700 includes a transparent tapered tip with planar wing-like protrusions or extensions disposed proximal to the distal end 1720 of the tip 1700. The wing-like protrusions 1702, 1704 each include a swept back leading edge. As shown in FIG. 17b, the tip 1200 is tilted away from the mounting rod 1404 to align with the central axis of an endoscopic lumen (not shown). The wing-like protrusions 1702, 1704 may also include curved distal and proximal edges, for example, in a parabolic configuration as shown in FIG. 17c, providing a smoother withdrawal of the cannula 100 from the insufflated tunnel. The tip 1700 attaches to the cannula body 100 in the same manner as previously described with reference to the offset tip 1200, with an elongated rod 1404 extending through a lumen of the cannula 100 and locking at the proximal end of the handle 1412. The cannula 100 may thus be advanced through tissue under full-field endoscopic visualization through the tapered tip 1720 with the wing-like protrusions 1702, 1704 extending substantially diametrically to facilitate tunnel dilation.

The wing-like protrusions 1702, 1704 of the tip 1700 are arranged in substantially planar geometry in contrast to the solid bulbous, oval element described above. The planar configuration of the wing-like protrusions 1702, 1704 substantially reduce the frontal profile of the dilator required to penetrate tissue, and thus reduces the resistive force encountered during advancement of the cannula 100 through tissue. Although the tissue-dilating force is exerted on tissue surrounding the cavity in a bilateral, substantially planar orientation by the outer edges of the wing-like protrusions 1702, 1704 that dissect tissue forming the cavity walls, the dilated cavity may retain a round cross-section for example, within an insufflated cavity, in the same manner as if tissue dilation was performed using a solid oval dilator that applies dilating force circumferentially.

Figure 18:
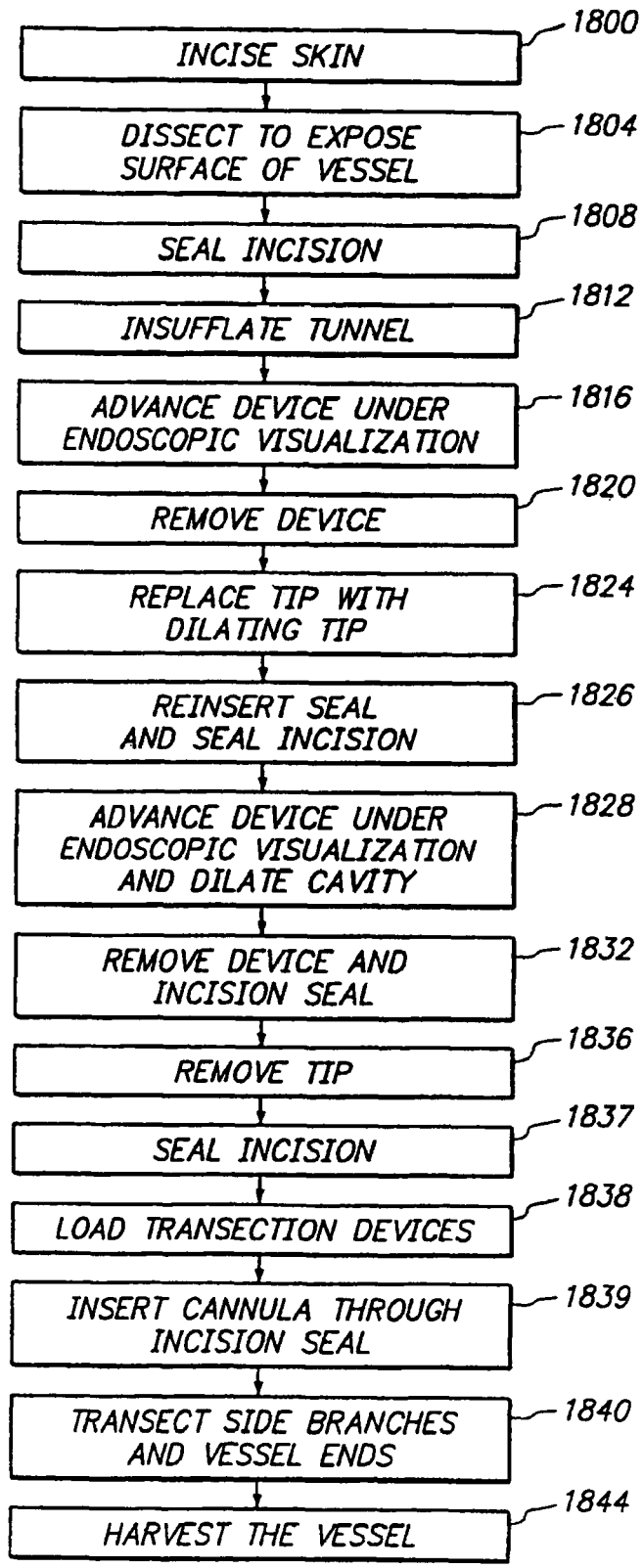
FIG. 18 is a flow chart illustrating a method of dilating tissue in accordance with the present invention.

FIG. 18 illustrates a method of dilating tissue in accordance with one method embodiment of the present invention. The skin is incised 1800 overlying the vessel of interest, and the scissor tool is inserted into the incision to create a path to the vessel by dissecting the overlying tissue. The incision is then bluntly dissected 1804 using the offset tip 1200 to expose the vessel surface. The incision is sealed 1808 and a tunnel is insufflated 1812. The cannula 100 is advanced 1816 along the vessel under endoscopic visualization through the transparent tip 1200. After sufficient length of tunnel is formed adjacent the vessel, the cannula 100 is removed 1820 and the incision seal is removed or slid backwards to the proximal end of the cannula 100. The offset tip 1200 is then replaced 1824 with the dilating tip 1700. The seal is reinserted and the incision is sealed 1826. The cannula 100 is advanced 1828 and the cavity is further dilated responsive to the advancement of the planar wing-like protrusions 1702, 1704 through tissue forming the tunnel walls. The cannula 100 is removed 1832 a second time, and the incision seal is again removed or slid backwards to the proximal end of the cannula 100. The dilating tip is removed 1836 and the incision is sealed 1837. Transection devices are loaded 1838 through instrument lumens within the cannula body 100 into the cannula 100 and the cannula 100 is then inserted 1839 back into the incision. Without any tip covering the distal end of the cannula 100, the vessel side branches and ends are transected 1840 using endoscopic instruments, and the vessel is then removed 1844 from the dilated tunnel.

What is claimed is:

1. A surgical apparatus comprising:
an elongated cannula having a lumen extending therein between proximal and distal ends;
a retractor disposed to slide within the lumen to extend a distal end thereof beyond the distal end of the cannula;
an angling device connected to the retractor near the distal end of the retractor and extending within the cannula toward the proximal end thereof for selectively deflecting the distal end of the retractor away from a central axis of the cannula in response to manual manipulation of the angling device from near the proximal end of the cannula;
wherein the distal end of the retractor is configured to move, upon extension, an object away from the central axis of the cannula.

2. The surgical apparatus of claim 1, wherein a movement of at least a part of the retractor relative to the cannula is not parallel to the central axis.

3. The surgical apparatus of claim 1, wherein when the distal end of the retractor is extended beyond the distal end of the cannula, the elongated cannula provides access for a surgical tool to cooperate with the retractor to perform a surgical operation at a surgical site.

4. The surgical apparatus of claim 3, further comprising the surgical tool, the surgical tool configured to perform the surgical procedure at a location distal to the distal end of the cannula when the distal end of the retractor is extended beyond the distal end of the cannula.

5. The surgical apparatus according to claim 1 in which the angling device includes a tension member extending within the cannula from attachment to the retractor beyond the distal end of the cannula, to a handle disposed near the proximal end of the cannula for selectively exerting tension on the retractor to deflect a portion of the retractor extended beyond the distal end of the cannula in response to manual pull applied to the handle relative to the cannula.

6. The surgical apparatus according to claim 5, further comprising an auxiliary lumen extending within the cannula between distal and proximal ends thereof, wherein the tension member extends through the auxiliary lumen.

7. The surgical apparatus according to claim 5, wherein the distal portion of the retractor is resiliently flexible for deflection in response to pull exerted thereon by the tension member.

8. The surgical apparatus according to claim 5, wherein the retractor is disposed to engage a vessel structure for selectively displacing the vessel structure in response to tensile force exerted on the retractor through the tension member.

9. A surgical apparatus comprising:
- an elongated cannula having a proximal end, a distal end, and a lumen extending between the proximal and distal ends;
- a visualization tool located near the distal end of the elongated cannula;
- a retractor having a distal end, the retractor disposed to slide within the lumen of the elongated cannula to extend the distal end of the retractor beyond the distal end of the cannula; and
- an angling device connected near the distal end of the retractor and extending within the cannula toward the proximal end of the cannula, the angling device configured for selectively deflecting the distal end of the retractor away from a central axis of the cannula in response to manual manipulation of the angling device from near the proximal end of the cannula;
- wherein when the retractor is not extended, the distal end of the retractor is adjacent to the visualization tool and at least partially encompasses the visualization tool.

10. The surgical apparatus of claim 9, wherein the distal end of the retractor has a first concave region that at least partially encompasses the visualization tool when the retractor is not extended.

11. The surgical apparatus of claim 10, wherein the retractor has a second concave region on an opposite side of distal end of the retractor from the first concave region.

12. The surgical apparatus of claim 9, wherein the visualization tool is an endoscope.

13. The surgical apparatus of claim 9, wherein the retractor allows a clear field of view of a surgical site by the visualization tool beyond the cannula upon extension of the retractor beyond the distal end of the cannula.

14. The surgical apparatus of claim 9, wherein the retractor, when extended, is configured to be used with a different surgical tool during a surgical procedure.

* * * * *